United States Patent
Hoffmann et al.

(10) Patent No.: US 7,625,899 B2
(45) Date of Patent: Dec. 1, 2009

(54) PYRIDODIHYDROPYRAZIONES, PROCESS FOR THEIR MANUFACTURE AND USE THEREOF AS MEDICAMENTS

(75) Inventors: Matthias Hoffmann, Mittelbiberach (DE); Matthias Grauert, Biberach (DE); Trixi Brandl, Warthausen (DE); Martin Steegmaier, Vienna (AT); Rudolf Hauptmann, Ebreichdorf (AT)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 327 days.

(21) Appl. No.: 11/176,737

(22) Filed: Jul. 7, 2005

(65) Prior Publication Data

US 2006/0009457 A1   Jan. 12, 2006

(30) Foreign Application Priority Data

Jul. 9, 2004   (DE) ........................ 10 2004 033 670

(51) Int. Cl.
| | | |
|---|---|---|
| A01N 43/58 | (2006.01) | |
| A01N 43/60 | (2006.01) | |
| A61K 31/50 | (2006.01) | |
| A61K 31/495 | (2006.01) | |
| C07D 237/00 | (2006.01) | |
| C07D 239/00 | (2006.01) | |
| C07D 241/00 | (2006.01) | |
| C07D 471/00 | (2006.01) | |
| C07D 487/00 | (2006.01) | |
| C07D 491/00 | (2006.01) | |
| C07D 495/00 | (2006.01) | |
| C07D 497/00 | (2006.01) | |

(52) U.S. Cl. .................. 514/249; 544/230; 544/350
(58) Field of Classification Search .................. None
See application file for complete search history.

(56) References Cited

U.S. PATENT DOCUMENTS

| | | | |
|---|---|---|---|
| 4,957,922 | A | 9/1990 | Lammens et al. |
| 5,167,949 | A | 12/1992 | Ferrand et al. |
| 5,424,311 | A | 6/1995 | Billhardt-Troughton et al. |
| 5,698,556 | A | 12/1997 | Chan |
| 6,174,895 | B1 | 1/2001 | Kleinman |
| 6,605,255 | B2 | 8/2003 | Kroll et al. |
| 6,806,272 | B2 | 10/2004 | Bauer et al. |
| 7,238,807 | B2 | 7/2007 | Duran et al. |
| 7,241,889 | B2 | 7/2007 | Hoffmann et al. |
| 7,332,491 | B2 | 2/2008 | Grauert et al. |
| 7,371,753 | B2 | 5/2008 | Stadtmueller et al. |
| 2002/0183292 | A1 | 12/2002 | Pairet et al. |
| 2002/0183293 | A1 | 12/2002 | Banerjee et al. |
| 2003/0130286 | A1 | 7/2003 | Denny et al. |
| 2004/0029885 | A1 | 2/2004 | Bauer et al. |
| 2004/0147524 | A1 | 7/2004 | Bauer et al. |
| 2004/0176380 | A1 | 9/2004 | Hoffmann et al. |
| 2005/0014760 | A1 | 1/2005 | Hoffmann et al. |
| 2005/0014761 | A1 | 1/2005 | Hoffmann et al. |
| 2005/0148501 | A1 | 7/2005 | Palmer et al. |
| 2005/0159414 | A1 | 7/2005 | Nickolaus et al. |
| 2005/0165010 | A1 | 7/2005 | Nickolaus et al. |
| 2006/0004014 | A1 | 1/2006 | Hoffmann et al. |
| 2006/0009457 | A1 | 1/2006 | Hoffmann et al. |
| 2006/0025411 | A1 | 2/2006 | Hoffmann et al. |
| 2006/0035902 | A1 | 2/2006 | Linz et al. |
| 2006/0035903 | A1 | 2/2006 | Mohr et al. |
| 2006/0046989 | A1 | 3/2006 | Grauert et al. |
| 2006/0047118 | A1 | 3/2006 | Stadtmueller et al. |

(Continued)

FOREIGN PATENT DOCUMENTS

| | | |
|---|---|---|
| WO | WO 01/19825 A1 | 3/2001 |
| WO | WO 02/076954 A1 | 10/2002 |
| WO | WO 02/076985 A1 | 10/2002 |
| WO | WO 03/020722 A1 | 3/2003 |
| WO | WO 2004/076454 A1 | 9/2004 |

OTHER PUBLICATIONS

Dorwald F. A. Side Reactions in Organic Synthesis, 2005, Wiley: VCH, Weinheim p. IX of Preface.*

(Continued)

*Primary Examiner*—James O Wilson
*Assistant Examiner*—Jeffrey H Murray
(74) *Attorney, Agent, or Firm*—Michael P. Morris; Mary-Ellen M. Devlin; Anthony P. Bottino

(57) ABSTRACT

Disclosed are pyridodihydropyrazinone compounds, processes for preparing them and their use as pharmaceutical compositions. The compounds according to the invention correspond to general formula (I),

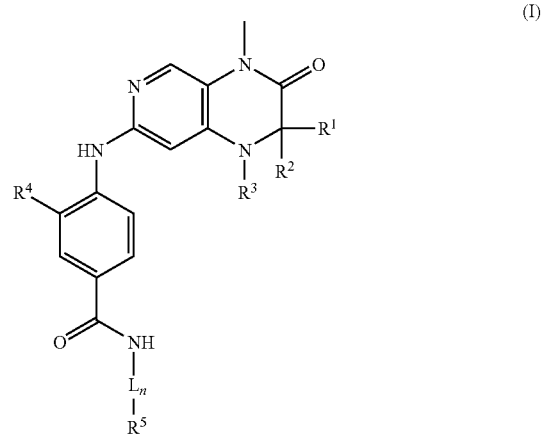

while the groups L, $R^1$, $R^2$, $R^3$, $R^4$ and $R^5$ may have the meanings given in the claims and specification.

13 Claims, No Drawings

U.S. PATENT DOCUMENTS

| | | | |
|---|---|---|---|
| 2006/0052383 | A1 | 3/2006 | Grauert et al. |
| 2006/0058311 | A1 | 3/2006 | Munzert et al. |
| 2006/0074088 | A1 | 4/2006 | Munzert et al. |
| 2006/0079503 | A1 | 4/2006 | Schwede et al. |
| 2008/0108812 | A1 | 5/2008 | Grauert et al. |
| 2008/0113992 | A1 | 5/2008 | Grauert et al. |
| 2008/0171747 | A1 | 7/2008 | Hoffman et al. |
| 2008/0177066 | A1 | 7/2008 | Linz et al. |
| 2008/0194818 | A1 | 8/2008 | Grauert et al. |
| 2008/0293944 | A1 | 11/2008 | Hoffmann et al. |
| 2009/0143379 | A1 | 6/2009 | Mohr et al. |

OTHER PUBLICATIONS

Vippagunta et. al. Advanced Drug Delivery Reviews 48 (2001) 3-26.*

Tenbrink, R. E. et al., "Antagonist, partial agonist, and full agonist imidazo[1,5-a]quinoxaline amides and carbamates acting through the BABA/Benzodiazepine receptor". J. Med. Chem. 1994, 37, pp. 758-768.

Turner, W.W.et al., "Recent advances in the medicinal chemistry of antifungal agents". Current Pharmacutical Design, 1996, 2, pp. 209-224.

Verschuren, E.W. et al., "The cell cycle and how it is steered by Kaposi's sarcoma-associated herpesvirus cyclin". Journal of General Virology, 2004, 85, pp. 1347-1361.

Viral Defense Foundation. www.viraldefense.org/mission.htm, downloaded Mar. 26, 2009.

Visiting Nurse Association of America. www.vnaa.org/gen/Germ_Protection_Center_Cold_and_Flu_Resources,html, downloaded Mar. 26, 2009.

Voskoglou-Nomikos, T. et al., "Clinical predictive value of the in vitro cell line, human xenograft, and mouse allograft preclinical cancer models". Clinical Cancer Research vol. 9, 2003, pp. 4227-4239.

Webster's Comprehensive Dictionary, 1996, pp. 1013-1014.

Wolf, D. E.et al., "The structure of rhizopterin". Contribution from the Research Labs of Merck and Co. Inc. Nov. 1947, Journal of American Chem. Soc., vol. 69, pp. 2753-2759. XP002352205.

Ghandi, L, et al., "An Open-Label Phase II Trial of the PLK Inhibitor BI 2536 in Patients with Sensitive Relapse Small Cell Lung Cancer". ASCO Meeting 2009.

Wagner, B. et al, "7-Benzylamino-6-chloro-2-piperazino-4-pyrrolidino-pteridine, a potent inhibitor of cAMP-specific phosphodiesterase, enhancing nuclear protein binding to the CRE consensus sequence in human tumour cells", Biochemical Pharmacology, Pergamon, Oxford, GB, 2002, pp. 659-668.

Wagner, G. et al., "Synthesis of new pluido[3',2':4,5] thieno '3,2-d] 1,2,3-triazine derivatives as antianaphylactics". Biosciences Dept of the University of Leipzig, Pharmazie (Pharmacy), 48, vol. 7, 1993, pp. 514-518.

Wikipedia. "Melting Point", Jan 17, 2007.

* cited by examiner

PYRIDODIHYDROPYRAZIONES, PROCESS FOR THEIR MANUFACTURE AND USE THEREOF AS MEDICAMENTS

APPLICATION DATA

This case claims priority to German application DE 10 2004 033670.9 filed Jul. 9, 2004.

The present invention relates to new pyridodihydropyrazinone, processes for the preparation thereof and the use thereof as pharmaceutical compositions. The compounds according to the invention correspond to general formula (I),

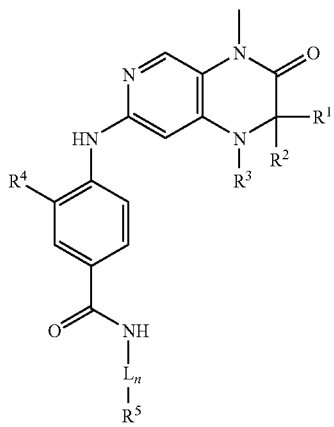

while the groups L, $R^1$, $R^2$, $R^3$, $R^4$ and $R^5$ may have the meanings given in the claims and specification.

BACKGROUND TO THE INVENTION

Dihydro-pteridinone derivatives (WO 03/020722) and pyrido[3,4-b]pyrazinones (WO 2002/076954) are known from the prior art as active substances with an antiproliferative activity.

Tumour cells wholly or partly elude regulation and control by the body and are characterised by uncontrolled growth. This is based on the one hand on the loss of control proteins, such as e.g. Rb, p16, p21 and p53 and also on the activation of so-called accelerators of the cell cycle, the cyclin-dependent kinases (CDK's).

In addition, the protein kinase Aurora B has been described as having an essential function during entry into mitosis. Aurora B phosphorylates histone H3 at Ser10 and thus initiates chromosome condensation (Hsu et al. 2000, *Cell* 102: 279-91). A specific cell cycle arrest in the G2/M phase may however also be triggered e.g. by the inhibition of specific phosphatases such as e.g. Cdc25C (Russell and Nurse 1986, *Cell* 45:145-53). Yeasts with a defective Cdc25 gene arrest in the G2 phase, while overexpression of Cdc25 leads to premature entry into the mitosis phase (Russell and Nurse 1987, *Cell* 49:559-67). Moreover, an arrest in the G2/M phase may also be triggered by the inhibition of certain motor proteins, the so-called kinesins such as e.g. Eg5 (Mayer et al. 1999, *Science* 286:971-4), or by agents which stabilise or destabilise microtubules (e.g. colchicin, taxol, etoposide, vinblastin, vincristine) (Schiff and Horwitz 1980, *Proc Natl Acad Sci USA* 77:1561-5).

In addition to the cyclin-dependent and Aurora kinases the so-called polo-like kinases, a small family of serine/threonine kinases, play an important part in the regulation of the eukaryotic cell cycle. Hitherto, the polo-like kinases PLK-1, PLK-2, PLK-3 and PLK-4 have been described in the literature. PLK-1 in particular has been shown to play a central part in the regulation of the mitosis phase. PLK-1 is responsible for the maturation of the centrosomes, for the activation of phosphatase Cdc25C, and for the activation of the Anaphase Promoting Complex (Glover et al. 1998, *Genes Dev.* 12:3777-87; Qian et al. 2001, *Mol Biol Cell.* 12:1791-9). The injection of PLK-1 antibodies leads to a G2 arrest in untransformed cells, whereas tumour cells arrest in the mitosis phase (Lane and Nigg 1996, *J Cell Biol.* 135:1701-13). Overexpression of PLK-1 has been demonstrated for various types of tumour, such as non-small-cell lung cancer, plate epithelial carcinoma, breast and colorectal carcinoma (Wolf et al. 1997, *Oncogene* 14:543-549; Knecht et al. 1999, *Cancer Res.* 59:2794-2797; Wolf et al. 2000, *Pathol. Res. Pract.* 196:753-759; Takahashi et al. 2003, *Cancer Sci.* 94:148-52). Therefore, this category of proteins also constitutes an interesting approach to therapeutic intervention in proliferative diseases (Liu and Erikson 2003, *Proc Natl Acad Sci USA* 100:5789-5794).

The resistance of many types of tumours calls for the development of new pharmaceutical compositions for combating tumours.

The aim of the present invention is to provide new compounds having an antiproliferative activity.

DETAILED DESCRIPTION OF THE INVENTION

Surprisingly it has been found that compounds of general formula (I) wherein the groups L and $R^1$ to $R^5$ have the meanings given hereinafter act as inhibitors of specific cell cycle kinases. The compounds named have an antiproliferative activity, in that they arrest cells in the mitosis phase of the cell cycle before programmed cell death is initiated in the arrested cells. Thus, the compounds according to the invention may be used for example to treat diseases connected with the activity of specific cell cycle kinases and characterised by excessive or abnormal cell proliferation.

(A1) The present invention therefore relates to compounds of general formula (I)

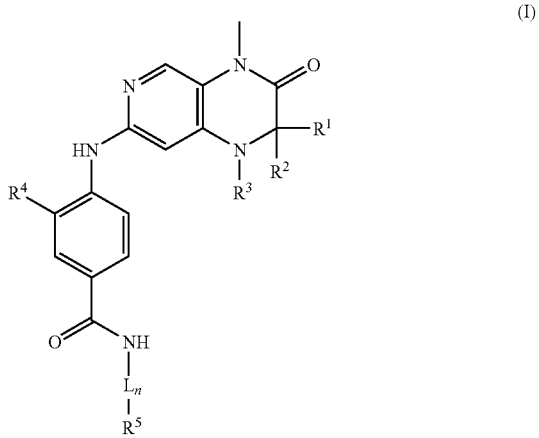

wherein $R^1$, $R^2$ which may be identical or different denote hydrogen or a group selected from among optionally substituted $C_1$-$C_6$-alkyl, $C_2$-$C_6$-alkenyl and $C_2$-$C_6$-alkynyl, or $R^1$ and $R^2$ together denote a 2- to 5-membered alkyl bridge, $R^3$ denotes hydrogen or a group selected from among optionally substituted $C_1$-$C_{12}$-alkyl, $C_2$-$C_{12}$-alkenyl, $C_2$-$C_{12}$-alkynyl and $C_6$-$C_{14}$-aryl, or a group selected from among optionally substituted and/or bridged $C_3$-$C_{12}$-cycloalkyl, $C_3$-$C_{12}$-cycloalkenyl, $C_7$-$C_{12}$-polycycloalkyl, $C_7$-$C_{12}$-polycycloalkenyl and $C_5$-$C_{12}$-spirocycloalkyl, $R^4$ denotes a group selected from among hydrogen, hydroxy and halogen, or a group selected from among optionally substituted $C_1$-$C_3$-alkyl, $C_2$-$C_6$-alkenyl, $C_2$-$C_6$-alkynyl, $C_1$-$C_5$-alkyloxy, $C_2$-$C_5$-alkenyloxy and $C_2$-$C_5$-alkynyloxy, L denotes a linker selected from among optionally substituted $C_2$-$C_{10}$-alkyl, $C_2$-$C_{10}$-alkenyl, $C_6$-$C_{14}$-aryl, —$C_1$-$C_4$-alkyl-$C_6$-$C_{14}$-aryl, $C_6$-$C_{14}$-heteroaryl, optionally bridged $C_3$-$C_{12}$-cycloalkyl, n denotes 0 or 1, $R^5$ denotes a group selected from among hydrogen or optionally substituted $C_1$-$C_6$-alkyl, $C_1$-$C_6$-alkenyl, $C_1$-$C_6$-alkynyl, $C_3$-$C_{12}$-cycloalkyl, or a group selected from among optionally substituted pyridyl, morpholinyl, piperidinyl, piperazinyl, piperazinylcarbonyl, pyrrolidinyl, tropenyl, sulphoxomorpholinyl, sulphonylmorpholinyl, thiomorpholinyl and azacycloheptyl, optionally in the form of the tautomers, the racemates, the enantiomers, the diastereomers and the mixtures thereof, and optionally the pharmacologically acceptable acid addition salts, solvates or hydrates, preferably the mono- or dihydrates thereof.

Preferred are compounds of formula (I) wherein $R^3$ to $R^5$, n and L are as hereinbefore defined, and $R^1$, $R^2$ which may be identical or different denote hydrogen, or a group selected from among methyl, ethyl, propyl, propargyl and allyl, or $R^1$ and $R^2$ together denote cyclopropyl.

Also preferred are compounds of formula (I), wherein $R^1$ to $R^4$, n and L are as hereinbefore defined, and $R^5$ denotes a group selected from among hydrogen or optionally substituted $C_1$-$C_6$-alkyl, $C_3$-$C_{12}$-cycloalkyl, or a group selected from among optionally substituted pyridyl, morpholinyl, piperidinyl, piperazinyl and piperazinylcarbonyl.

Particularly preferred are compounds of formula (I) wherein $R^1$, $R^2$, $R^4$, $R^5$, n and L are as hereinbefore defined, and $R^3$ denotes hydrogen, optionally substituted $C_1$-$C_6$-alkyl or optionally substituted and/or bridged $C_3$-$C_{12}$-cycloalkyl.

Particularly preferred are compounds of formula (I), wherein $R^1$, $R^2$, $R^3$, $R^5$, n and L are as hereinbefore defined, and $R^4$ denotes a group selected from among hydrogen, hydroxy, halogen, methyl, ethyl, propynyloxy and methoxy.

The invention further relates to compounds of formula I for use as pharmaceutical compositions.

Of particular importance according to the invention are compounds of formula I for use as pharmaceutical compositions with an antiproliferative activity.

The invention also relates to the use of a compound of formula I for preparing a pharmaceutical composition for the treatment and/or prevention of cancer, infections, inflammatory and autoimmune diseases.

The invention also relates to a method of treating and/or preventing cancer, infections, inflammatory and autoimmune diseases, characterised in that an effective amount of a compound of formula I is administered to a patient.

The invention also relates to pharmaceutical preparations, containing as active substance one or more compounds of general formula (I) or the physiologically acceptable salts thereof, optionally combined with conventional excipients and/or carriers.

The invention further relates to a process for preparing a compound of general formula (I),

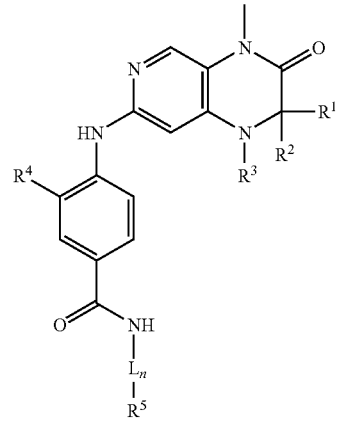

wherein $R^1$-$R^5$, n and L are as hereinbefore defined, characterised in that a compound of general formula (II)

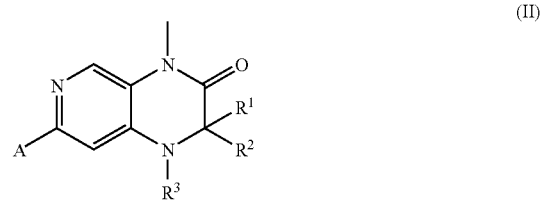

wherein $R^1$-$R^3$ have the meanings given above in 1 to 4 and A is a leaving group, is reacted with an optionally substituted compound of general formula (III),

wherein
R⁴ has the meaning given above in 1 to 5 and
R⁶ denotes OH, —O-methyl, —O-ethyl, to obtain a product of general formula (IV),

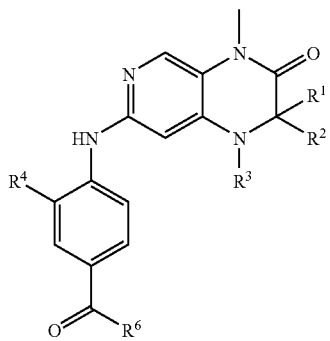

(IV)

wherein
R¹ to R⁴ are as hereinbefore defined and
R⁶ denotes OH, —NH-L$_n$-R⁵, —O-methyl or —O-ethyl, and then optionally the product of general formula (IV) obtained is reacted, optionally after previous hydrolysis of the ester group —COR⁶, with an amine of general formula (V)

  (V)

wherein
R⁵ is as hereinbefore defined.
The invention further relates to a compound of formula (II),

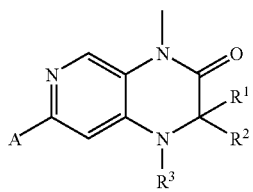

(II)

wherein
R¹-R³ are as hereinbefore defined and A is a leaving group.

The term alkyl groups, including alkyl groups which are a part of other groups, denotes branched and unbranched alkyl groups with 1 to 12 carbon atoms, preferably 1-6, most preferably 1-4 carbon atoms, such as, for example: methyl, ethyl, propyl, butyl, pentyl, hexyl, heptyl, octyl, nonyl and decyl. Unless otherwise stated, the abovementioned terms propyl, butyl, pentyl, hexyl, heptyl, octyl, nonyl, decyl and dodecyl include all the possible isomeric forms. For example, the term propyl includes the two isomeric groups n-propyl and iso-propyl, the term butyl includes n-butyl, iso-butyl, sec. butyl and tert.-butyl, the term pentyl includes iso-pentyl, neopentyl, etc.

In the abovementioned alkyl groups one or more hydrogen atoms may optionally be replaced by other groups. For example these alkyl groups may be substituted by fluorine. All the hydrogen atoms of the alkyl group may optionally also be replaced.

The term alkyl bridge, unless otherwise stated, denotes branched and unbranched alkyl groups with 2 to 5 carbon atoms, for example ethylene, propylene, isopropylene, n-butylene, iso-butyl, sec. butyl and tert.-butyl etc. bridges. Methylene, ethylene, propylene and butylene bridges are particularly preferred. In the alkyl bridges mentioned 1 to 2 C-atoms may optionally be replaced by one or more heteroatoms selected from among oxygen, nitrogen or sulphur.

The term alkenyl groups (including those which are a part of other groups) denotes branched and unbranched alkylene groups with 2 to 12 carbon atoms, preferably 2-6 carbon atoms, most preferably 2-3 carbon atoms, provided that they have at least one double bond. Examples include: ethenyl, propenyl, butenyl, pentenyl etc. Unless otherwise stated, the abovementioned terms propenyl, butenyl, etc also include all the possible isomeric forms. For example, the term butenyl includes 1-butenyl, 2-butenyl, 3-butenyl, 1-methyl-1-propenyl, 1-methyl-2-propenyl, 2-methyl-1-propenyl, 2-methyl-2-propenyl and 1-ethyl-1-ethenyl.

In the abovementioned alkenyl groups, unless otherwise stated, one or more hydrogen atoms may optionally be replaced by other groups. For example, these alkyl groups may be substituted by the halogen atom fluorine. All the hydrogen atoms of the alkenyl group may optionally also be replaced.

The term alkynyl groups (including those which are a part of other groups) denotes branched and unbranched alkynyl groups with 2 to 12 carbon atoms, provided that they have at least one triple bond, for example ethynyl, propargyl, butynyl, pentynyl, hexynyl etc., preferably ethynyl or propynyl.

In the abovementioned alkynyl groups, unless otherwise stated, one or more hydrogen atoms may optionally be replaced by other groups. For example, these alkyl groups may be substituted by fluorine. All the hydrogen atoms of the alkynyl group may optionally also be replaced.

The term aryl denotes an aromatic ring system with 6 to 14 carbon atoms, preferably 6 or 10 carbon atoms, preferably phenyl, which, unless otherwise stated, may carry one or more of the following substituents, for example: OH, NO₂, CN, OMe, —OCHF₂, —OCF₃, —NH₂, halogen, preferably fluorine or chlorine, C₁-C₁₀-alkyl, preferably C₁-C₅-alkyl, preferably C₁-C₃-alkyl, particularly preferably methyl or ethyl, —O—C₁-C₃-alkyl, preferably —O-methyl or —O-ethyl, —COOH, —COO—C₁-C₄-alkyl, preferably —COO-methyl or —COO-ethyl, or —CONH₂.

As heteroaryl groups wherein up to two C atoms are replaced by one or two nitrogen atoms are mentioned, for example, pyrrole, pyrazole, imidazole, triazole, pyridine, pyrimidine, while each of the above-mentioned heteroaryl rings may optionally also be anellated to a benzene ring, preferably benzimidazole, and these heterocycles, unless stated to the contrary, may for example carry one or more of the following substituents: F, Cl, Br, OH, OMe, methyl, ethyl, CN, CONH₂, NH₂, optionally substituted phenyl, optionally substituted heteroaryl, preferably optionally substituted pyridyl.

Examples of cycloalkyl groups are cycloalkyl groups with 3-12 carbon atoms, for example cyclopropyl, cyclobutyl, cyclopentyl, cyclohexyl, cycloheptyl or cyclooctyl, preferably cyclopropyl, cyclopentyl or cyclohexyl, while each of the above-mentioned cycloalkyl groups may optionally also carry one or more substituents, for example: OH, NO₂, CN, OMe, —OCHF$_2$, —OCF$_3$, —NH$_2$ or halogen, preferably fluorine or chlorine, C$_1$-C$_{10}$-alkyl, preferably C$_1$-C$_5$-alkyl, preferably C$_1$-C$_3$-alkyl, particularly preferably methyl or ethyl, —O—C$_1$-C$_3$-alkyl, preferably —O-methyl or —O-ethyl, —COOH, —COO-C$_1$-C$_4$-alkyl, preferably —COO-methyl or —COO-ethyl or —CONH$_2$. Particularly preferred substituents of the cycloalkyl groups are =O, OH, NH$_2$, methyl or F.

Examples of cycloalkenyl groups are cycloalkyl groups with 3-12 carbon atoms which have at least one double bond, for example cyclopropenyl, cyclobutenyl, cyclopentenyl, cyclohexenyl or cycloheptenyl, preferably cyclopropenyl, cyclopententyl or cyclohexenyl, while each of the above-mentioned cycloalkenyl groups may optionally also carry one or more substituents.

"=O" denotes an oxygen atom linked by a double bond.

Examples of polycycloalkyl groups are optionally substituted bi-, tri-, tetra- or pentacyclic cycloalkyl groups, for example pinane, 2.2.2-octane, 2.2.1-heptane or adamantane. Examples of polycycloalkenyl groups are optionally bridged and/or substituted 8- membered bi-, tri-, tetra- or pentacyclic cycloalkenyl groups, preferably bicycloalkenyl or tricycloalkenyl groups, if they contain at least one double bond, for example norbornene.

Examples of spiroalkyl groups are optionally substituted spirocyclic C$_5$-C$_{12}$ alkyl groups.

The term halogen generally denotes fluorine, chlorine, bromine or iodine, preferably fluorine, chlorine or bromine, particularly preferably chlorine.

By a leaving group A is meant a leaving group which may be identical or different such as for example —O-methyl, —SCN, fluorine, chlorine, bromine, iodine, methanesulphonyl, trifluoromethanesulphonyl or p-toluenesulphonyl, preferably chlorine.

The compounds according to the invention may be present in the form of the individual optical isomers, mixtures of the individual enantiomers, diastereomers or racemates, in the form of the tautomers and also in the form of the free bases or the corresponding acid addition salts with pharmacologically acceptable acids—such as for example acid addition salts with hydrohalic acids, for example hydrochloric or hydrobromic acid, or organic acids, such as for example oxalic, fumaric, diglycolic or methanesulphonic acid, as well as in the form of the solvates or hydrates, preferably mono- or dihydrates thereof.

The substituent R$^1$ or R$^2$ may represent hydrogen or a group selected from among optionally substituted C$_1$-C$_6$-alkyl, preferably methyl, ethyl or propyl particularly preferably methyl or ethyl, C$_2$-C$_6$-alkenyl, preferably allyl, 1-butenyl or 2-butenyl, particularly preferably allyl and C$_2$-C$_6$-alkynyl, preferably propynyl or butynyl, particularly preferably propynyl.

R$^1$ and R$^2$ may together denote a 2- to 5-membered alkyl bridge, preferably an ethylene, propylene or butylene bridge, which may contain 1 to 2 heteroatoms, preferably oxygen or nitrogen. Particularly preferably ethylene, propylene.

The substituent R$^3$ may represent hydrogen or a group selected from among optionally substituted C$_1$-C$_{12}$-alkyl, preferably propyl, butyl, pentyl, or hexyl, particularly preferably propyl, pentyl or hexyl, C$_2$-C$_{12}$-alkenyl, preferably butenyl, pentenyl or hexenyl, particularly preferably pentenyl or hexenyl, C$_2$-C$_{12}$-alkynyl, preferably propynyl, butynyl or pentynyl, particularly preferably butynyl or pentynyl and C$_6$-C$_{14}$-aryl, preferably phenyl or naphthalenyl, or a group selected from among optionally substituted and/or bridged C$_3$-C$_{12}$-cycloalkyl, preferably cyclopropyl, cyclobutyl, cyclopentyl or cyclohexyl, particularly preferably cyclopentyl or cyclohexyl, C$_3$-C$_{12}$-cycloalkenyl, preferably cyclopentenyl or cyclohexenyl, C$_7$-C$_{12}$-polycycloalkyl, preferably 2.2.1-heptanyl or adamantyl, C$_7$-C$_{12}$-polycycloalkenyl, preferably norbornenyl or C$_5$-C$_{12}$-spirocycloalkyl, preferably spiro[4.4]nonyl or spiro[2.4]heptyl.

Most preferably the substituent R$^3$ denotes isopentyl, isopropyl cyclohexyl or cyclopentyl.

The substituent R$^4$ may denote a group selected from among hydrogen, hydroxy and halogen, preferably fluorine, chlorine or bromine, particularly preferably fluorine or chlorine, or a group selected from among optionally substituted C$_1$-C$_3$-alkyl, preferably methyl, ethyl, or propyl, particularly preferably methyl or ethyl, C$_2$-C$_6$-alkenyl, preferably allyl, 2-butenyl or 2-pentenyl, particularly preferably allyl or 2-butenyl, C$_2$-C$_6$-alkynyl, preferably propynyl, 2-butynyl or 2-pentynyl, particularly preferably propynyl or 2-butynyl, C$_1$-C$_5$-alkyloxy, preferably methoxy, ethoxy or propyloxy, particularly preferably methoxy or ethoxy, C$_2$-C$_5$-alkenyloxy, preferably allyloxy, 2-butenyloxy or 2-pentenyloxy, particularly preferably allyloxy or 2-butenyloxy and C$_2$-C$_5$-alkynyloxy, preferably 2-propynyloxy, 2-butynyloxy or 2-pentynyloxy, particularly preferably 2-propynyloxy or 2-butynyloxy.

Particularly preferably the substituent R$^4$ denotes methoxy or ethyl.

L may denote a linker selected from among optionally substituted C$_2$-C$_{10}$-alkyl, preferably ethyl, propyl, butyl or pentyl, C$_2$-C$_{10}$-alkenyl, C$_6$-C$_{14}$-aryl, preferably phenyl, —C$_2$-C$_4$-alkyl-C$_6$-C$_{14}$-aryl, —C$_6$-C$_{14}$-aryl-C$_1$-C$_4$-alkyl, preferably—phenyl-methyl, optionally bridged C$_3$-C$_{12}$-cycloalkyl, preferably cyclohexyl, and heteroaryl, which contains 1 or 2 nitrogen atoms.

n denotes 0 or 1, preferably 1.

R$^5$ may represent a group selected from among hydrogen or optionally substituted C$_1$-C$_6$-alkyl, preferably methyl, ethyl or benzyl, particularly preferably methyl or ethyl, or a group selected from among optionally substituted pyridyl, morpholinyl, piperidinyl, piperazinyl, piperazinylcarbonyl, pyrrolidinyl, tropenyl, sulphoxomorpholinyl, sulphonylmorpholinyl, thiomorpholinyl and azacycloheptyl, preferably piperazinyl, piperidinyl, morpholinyl or pyrrolidinyl, particularly preferably piperazinyl or piperidinyl.

The substituent R$^6$ may represent OH, —O-methyl, —O-ethyl, preferably —O-methyl or —O-ethyl.

All the groups mentioned in the definitions of R$^1$ to R$^6$ may optionally be branched and/or substituted.

The compounds according to the invention may be prepared according to the methods of synthesis described below, while the substituents of general formulae (X1) to (X12) have the above-mentioned meanings. These processes are to be understood as illustrating the invention without restricting it to their content.

The compounds of general formula (I) may be prepared according to the following synthesis plan (I):

The compounds X1, X2 and X7 (R4=H; R=Et (X7a) and R4=OMe; R=Me (X7b)) are commercially obtainable; the compound X7c with R4=OMe and R=Et may be prepared by methods known from the literature: (a) Taran, F.; Renard, P. Y.; Bernard, H.; Mioskowski, C.; Frobert, Y.; et al.; *J. Amer. Chem. Soc.* 1998, 120, 3332-3339. (b) Ismail, Ibrahim A.; Sharp, Dale E.; Chedekel, Miles R.; *J. Org. Chem.* 1980, 45, 2243-2246.

Plan (I)
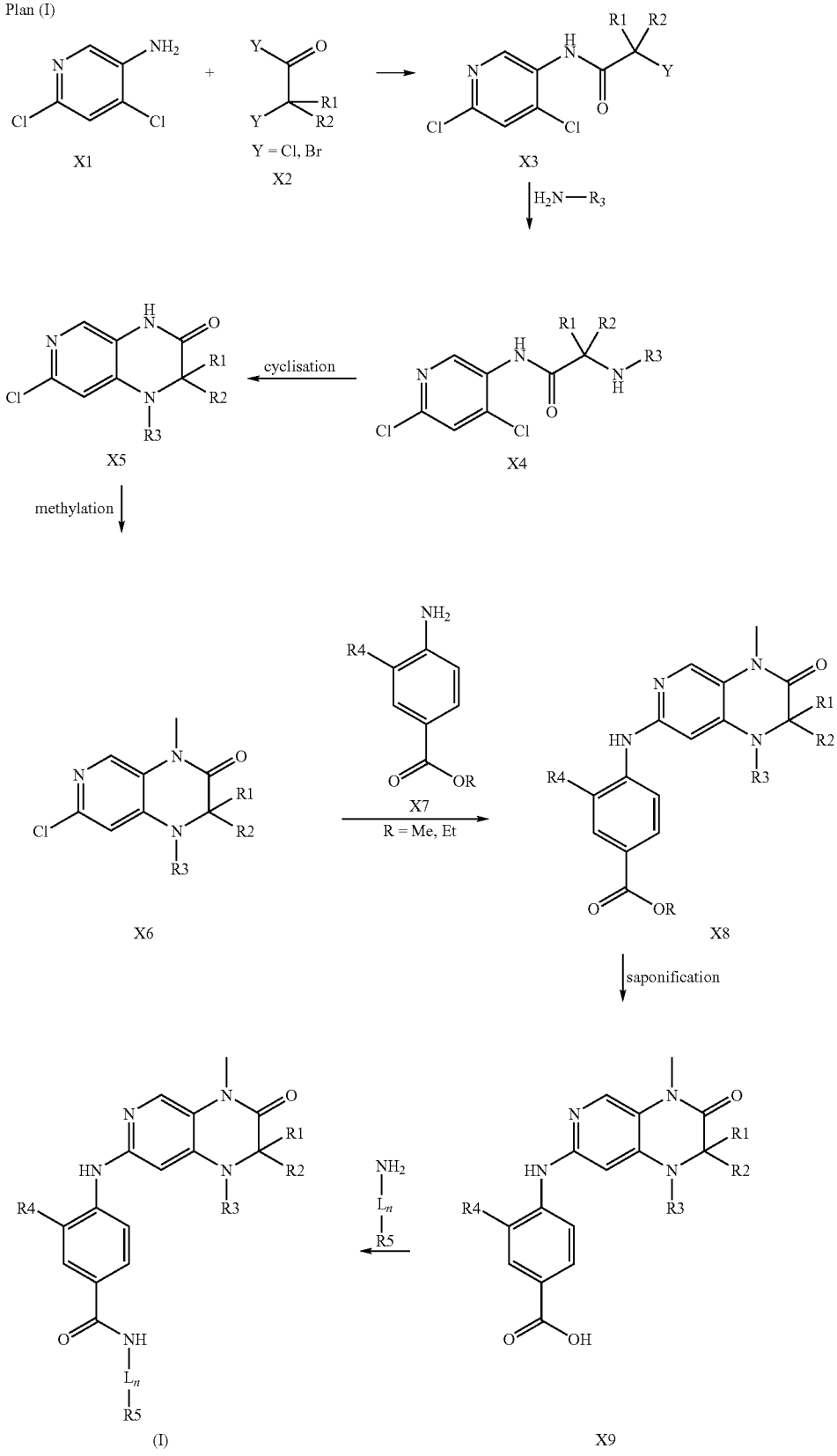

Alternatively the following method of synthesis may be used, which is particularly suitable for the preparation of enantiomerically pure compounds (Diagram (II)):
Compounds of type X10 may be prepared by methods known from the literature: Lundquist, Joseph T.; Pelletier, IV and Jeffrey C, *Org. Lett.* 2001, 3, 781. Freudenberg; Kuhn; Bumann, *Chem. Ber.* 1930, 63, 2385.
Plan (II)
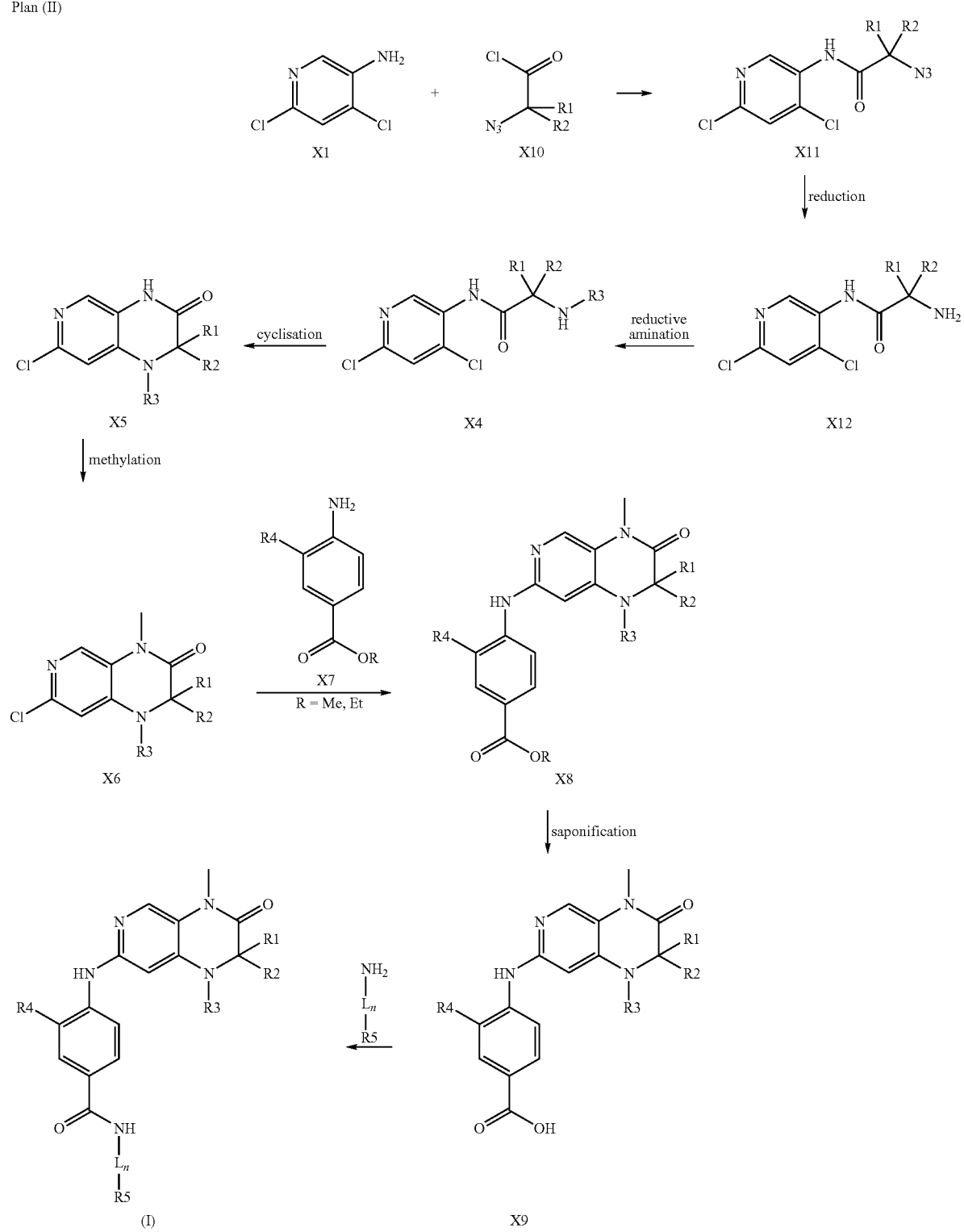

The new compounds of general formula (I) may be prepared analogously to the following examples of synthesis. These Examples are intended only as examples of methods to illustrate the invention without restricting it to their contents.

The preparation of some intermediate compounds used to synthesise the Examples is described hereinafter.

Intermediate Compound 1:

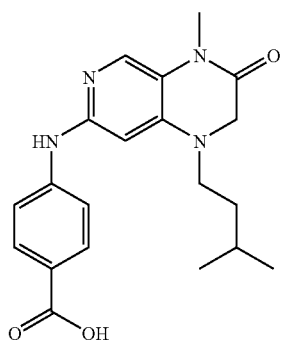

X9a 11.8 g 4,6-dichloro-pyridin-3-yl-amine dihydrochloride were placed in 200 mL dichloromethane and 200 mL water and combined with 30.0 g (215 mmol) potassium carbonate. The reaction mixture was cooled to 0° C. and 11.3 g (100 mmol) chloroacetyl chloride was added dropwise. After 30 minutes the organic phase was separated off and evaporated down. The residue was crystallised with ether.

Yield: 8.6 g of a compound X3a (colourless solid)

8.5 g of the compound X3a were placed in 85 mL dimethylformamide and combined with 13.9 g (100 mmol) potassium carbonate and 8.2 mL (71 mmol) 3-methylbutylamine. The reaction mixture was stirred for 2 hours at 50° C., then diluted with water. The aqueous phase was extracted twice with ethyl acetate. The combined organic phases were dried over $Na_2SO_4$ and evaporated down, the residue was taken up in methanol and crystallised with ethereal hydrochloric acid solution.

Yield: 8.5 g of a compound X4a (colourless solid)

8.4 g of the compound X4a were dissolved in 80 mL dimethylformamide, combined with 17.1 mL (100 mmol) N-ethyldiisopropylamine and heated to 100° C. for 2 hours. The reaction mixture was diluted with water and the aqueous phase was extracted twice with dichloromethane. The combined organic phases were dried over $Na_2SO_4$ and evaporated down. The residue was crystallised from ether.

Yield: 6.2 g of a compound X5a (colourless solid)

6.2 g of the compound X5a were placed in 30 mL dimethylacetamide and combined with 2.4 mL (37 mmol) methyl iodide. At −10° C. 1.3 g (30 mmol) sodium hydride were added batchwise as a 60% dispersion in mineral oil. After 30 minutes the reaction mixture was poured onto ice water. The precipitated precipitate was suction filtered, dissolved in ether, dried over $Na_2SO_4$ and evaporated down. The residue was crystallised from diisopropylether/petroleum ether.

Yield: 5.9 g of a compound X6a (colourless solid)

A suspension of 2.7 g of the compound X6a and 2.5 g (15 mmol) ethyl 4-aminobenzoate X7a in 20 mL toluene was combined with 0.6 g (1 mmol) 2,2'-bis-(diphenylphosphino)-1,1'-binaphthyl, 0.46 g (0.5 mmol) tris(dibenzylideneacetone)-dipalladium(0) and 6.5 g (20 mmol) caesium carbonate and stirred for 30 hours at 100° C. The reaction mixture was diluted with 50 mL ethyl acetate and 50 mL water and the precipitated solid was suction filtered. The organic phase of the filtrate was dried over $Na_2SO_4$ and evaporated down. The residue remaining was purified by column chromatography (eluant: dichloromethane/methanol 9:1).

Yield: 2.8 g of a compound X8a (yellow solid)

3 g of the compound X8a were dissolved in 100 mL methanol, combined with 15 mL 2N aqueous sodium hydroxide solution and heated to 60° C. for 2 hours. The reaction mixture was acidified with aqueous hydrochloric acid and the methanol was eliminated in vacuo. The precipitate formed was suction filtered and washed with water and acetone.

Yield: 2.4 g of a compound X9a (colourless solid)

Intermediate Compound 2:

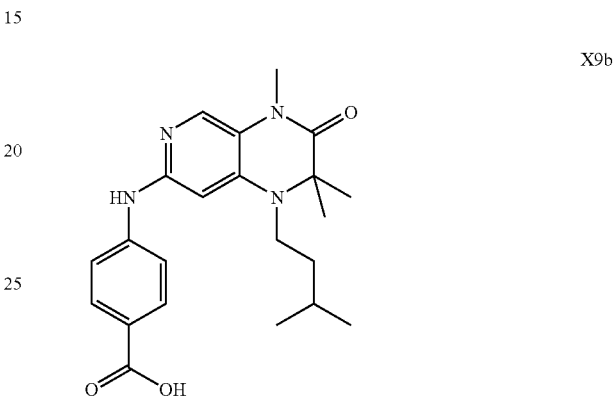

X9b 50 g (0.36 mol) potassium carbonate were dissolved in 400 mL water and 400 mL ether and combined with 20 g of 4,6-dichloro-pyridin-3-yl-amine dihydrochloride. The reaction mixture was cooled to 0° C. and a solution of 18.9 mL (0.15 mol) 2-bromo-isobutyric acid bromide was added dropwise within 2.5 hours. After 2.5 hours a further 18.9 mL of 2-bromo-isobutyric acid bromide, dissolved in 150 mL ether, and 20 g potassium carbonate were added and the mixture was stirred for 1 hour. The reaction mixture was diluted with ethyl acetate and washed with water. The organic phase was separated off, dried over $Na_2SO_4$ and evaporated down. The residue was purified by column chromatography (eluant: cyclohexane/ethyl acetate 100:0→>90:10).

Yield: 20.6 g of a compound X3b (colourless solid)

20 g of the compound X3b were placed in 80 mL dimethylformamide and combined with 16 g (120 mmol) potassium carbonate and 31.6 mL (270 mmol) 3-methylbutylamine. The reaction mixture was stirred for 1.5 hours at 60° C., then diluted with water and dichloromethane. The organic phase was evaporated down, the residue was taken up in ether and the product was crystallised with ethereal hydrochloric acid solution. The solid obtained was taken up in potassium hydrogen carbonate solution, evaporated down and the residue was purified by column chromatography (eluant: cyclohexane/ethyl acetate 100:0->25:75).

Yield: 11.5 g of a compound X4b (yellow oil)

11 g of the compound X4b were dissolved in 165 mL dimethylformamide, combined with 22 mL (130 mmol) N-ethyldiisopropylamine and heated to 155° C. for 72 hours. The reaction mixture was evaporated down and the residue remaining was crystallised by the addition of water. The solid was washed with water and a little ether.

Yield: 6.2 g of a compound X5b (light-grey solid)

6.3 g of the compound X5b were dissolved in 30 mL dimethylacetamide and combined with 2.1 mL (33 mmol) methyl iodide. At −10° C. 1.2 g (27 mmol) sodium hydride were added batchwise as a 60% dispersion in mineral oil. The reaction mixture was slowly heated to ambient temperature and then poured onto ice water. The precipitate formed was suction filtered and washed with water and petroleum ether.

Yield: 6.0 g of a compound X6b (colourless solid)

A suspension of 2 g of the compound X6b and 1.7 g (10 mmol) ethyl 4-aminobenzoate X7a in 15 mL toluene was combined with 0.4 g (0.6 mmol) 2,2'-bis-(diphenylphosphino)-1,1'-binaphthyl, 0.31 g (0.3 mmol) tris(dibenzylideneacetone)-dipalladium(0) and 4.4 g (14 mmol) caesium carbonate and stirred for 35 hours at 100° C. The reaction mixture was diluted with 100 mL ethyl acetate and 50 mL water and the solid formed was filtered off. The organic phase was dried over Na$_2$SO$_4$ and evaporated down. The residue was combined with tert-butylmethylether and the solid obtained was suction filtered.

Yield: 1.2 g of a compound X8b (brown solid)

1.7 g of the compound X8b were dissolved in 50 mL methanol, combined with a solution of 1.6 g (40 mmol) sodium hydroxide in 10 mL water and heated to 60° C. for 1.5 hours. The reaction mixture was evaporated down and then combined with water. The precipitate formed was suction filtered and washed with ether and petroleum ether.

Yield: 1.5 g of a compound X9b (colourless solid)

Intermediate Compound 3:

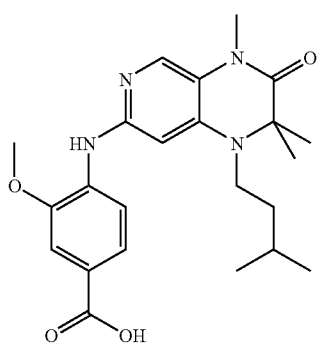

X9c

A suspension of 2 g of the compound X6b and 1.8 g (10 mmol) methyl 4-amino-3-methoxybenzoate X7b in 15 mL toluene was combined with 0.4 g (0.7 mmol) 2,2'-bis-(diphenylphosphino)-1,1'-binaphthyl, 0.3 g (0.3 mmol) tris(dibenzylideneacetone)-dipalladium(0) and 4.4 g (14 mmol) caesium carbonate and stirred for 30 hours at 100° C. The reaction mixture was diluted with 100 mL ethyl acetate and 50 mL water and the precipitated solid was suction filtered. The organic phase of the filtrate was dried over Na$_2$SO$_4$ and evaporated down. The residue remaining was purified by column chromatography (eluant: dichloromethane/methanol 9:1). The product was crystallised by the addition of ether.

Yield: 1.8 g of a compound X8c (brown solid)

1.8 g of the compound X8c were dissolved in 50 mL methanol, combined with a solution of 1.6 g (40 mmol) sodium hydroxide in 10 mL water and heated to 60° C. for 1.5 hours. The reaction mixture was evaporated down and then combined with water. The precipitate formed was suction filtered and washed with ether and petroleum ether.

Yield: 1.7 g of a compound X9c (colourless solid)

Intermediate Compound 4:

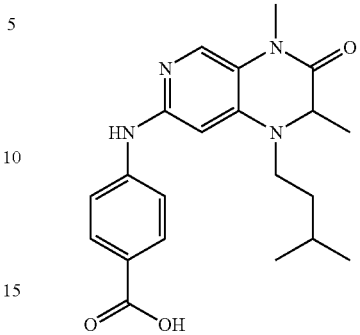

X9d 30.5 g 4,6-dichloro-pyridin-3-yl-amine dihydrochloride were placed in 400 mL ether and 300 mL ethyl acetate and combined at 0° C. with a solution of 75.9 g (0.55 mol) potassium carbonate in 250 mL water. Then 27.6 mL (0.26 mol) 2-bromopropionic acid bromide were added dropwise within 30 minutes and the reaction mixture was heated to ambient temperature within 2 hours. Any solids formed were filtered off and the filtrate was extracted with ethyl acetate. The combined organic phases were dried over Na$_2$SO$_4$, evaporated down and the product obtained was crystallised from ether.

Yield: 32.5 g of a compound X3d (colourless solid)

5.8 g of the compound X3d were placed in 50 mL dimethylformamide and combined with 5.2 g (38 mmol) potassium carbonate and 6 g (69 mmol) 3-methylbutylamine. The reaction mixture was stirred for 2 hours at 80° C. and then diluted with water. The aqueous phase was extracted twice with ethyl acetate. The combined organic phases were washed with water, dried over Na$_2$SO$_4$ and evaporated down. The residue was purified by flash column chromatography (eluant: cyclohexane/ethyl acetate 75:25).

Yield: 5.3 g of a compound X4d (colourless solid)

5.3 g of the compound X4d were dissolved in 10 mL dimethylformamide, combined with 4.3 g (20 mmol) tripotassium phosphate and heated to 125° C. for 3 hours. The reaction mixture was diluted with water and the aqueous phase was extracted twice with ethyl acetate. The combined organic phases were washed with water, dried over Na$_2$SO$_4$ and evaporated down. The residue was crystallised from petroleum ether.

Yield: 2.2 g of a compound X5d (colourless solid)

2.4 g of the compound X5d were placed in 15 mL dimethylacetamide and combined with 1 mL (16 mmol) methyl iodide. At −10° C., 0.5 g (13 mmol) sodium hydride were added batchwise as a 60% dispersion in mineral oil. After 15 minutes the reaction mixture was poured onto ice water and extracted twice with ether. The combined organic phases were dried over Na$_2$SO$_4$ and evaporated down. The residue was taken up in acetone and crystallised with ethereal hydrochloric acid solution.

Yield: 2.4 g of a compound X6d (colourless solid)

A suspension of 1.2 g of the compound X6d and 1.7 g (10 mmol) ethyl 4-aminobenzoate X7a in 15 mL toluene was combined with 0.3 g (0.5 mmol) 2,2'-bis-(diphenylphosphino)-1,1'-binaphthyl, 0.2 g (0.2 mmol) tris(dibenzylideneacetone)-dipalladium(0) and 5 g (15 mmol) caesium carbonate and refluxed for 18 hours. The reaction mixture was suction filtered through kieselguhr and evaporated down. The residue remaining was purified by column chromatography (eluant: dichloromethane/methanol 9:1). The product was taken up in acetone and precipitated as the hydrochloride using ethereal hydrochloric acid solution.

Yield: 0.9 g of a compound X8d (yellow solid)

0.9 g of the compound X8d were suspended in 15 mL water, combined with 15 mL semiconc. hydrochloric acid and refluxed for 2 hours. After cooling the precipitate formed was suction filtered and washed with water, acetone and ether.

Yield: 0.8 g of a compound X9d (colourless solid)

Intermediate Compound 5:

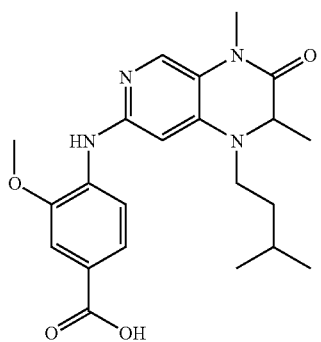

X9e

A suspension of 1.5 g of the compound X6d and 2.7 g (15 mmol) methyl 4-amino-3-methoxybenzoate X7b in 30 mL toluene was combined with 1.3 g (2 mmol) 2,2'-bis-(diphenylphosphino)-1,1'-binaphthyl, 0.9 g (1 mmol) tris(dibenzylideneacetone)-dipalladium(0) and 10 g (30 mmol) caesium carbonate and refluxed for 18 hours. After cooling the solid formed was suction filtered and the filtrate was evaporated down. The residue remaining was purified by column chromatography (eluant: dichloromethane/methanol 9:1).

Yield: 0.3 g of a compound X8e (brown solid)

0.3 g of the compound X8e were suspended in 10 mL 2N aqueous hydrochloric acid and refluxed for 2 hours. After cooling the precipitate formed was suction filtered and washed with water, acetone and ether.

Yield: 0.2 g of a compound X9e (colourless solid)

Intermediate Compound 6:

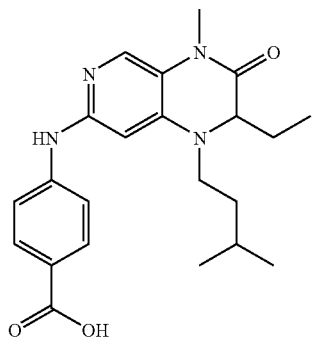

X9f 10 g 4,6-dichloro-pyridin-3-yl-amine were dissolved in 200 mL ether and combined with a solution of 20 g (0.14 mol) potassium carbonate. At 0° C. 15 mL (0.11 mol) 2-bromobutyryl bromide were added dropwise within two hours, during which time a solid formed. The reaction mixture was diluted with 200 mL ethyl acetate, the organic phase was dried over $Na_2SO_4$ and evaporated down.

The solid obtained was washed with ether.

Yield: 14.5 g of a compound X3f (colourless solid)

A mixture of 14.2 g of the compound X3f, 20 g (0.14 mol) potassium carbonate and 4.4 g (50 mmol) ) 3-methylbutylamine in 40 mL dimethylformamide was stirred for four hours at 120° C. and then evaporated down. The oil remaining was combined with water and extracted twice with ethyl acetate. The combined organic phases were washed with water, dried over $Na_2SO_4$ and evaporated down. The residue was taken up in ethyl acetate and the product was crystallised with ethereal hydrochloric acid. The solid obtained was washed with ethyl acetate and ether.

Yield: 10.2 g of a compound X4f (colourless solid)

A mixture of 11.7 g of the compound X4f and 10.3 g (80 mmol) of N-ethyldiisopropylamine in 50 mL dimethylformamide was refluxed for 9 hours. The reaction mixture was evaporated down, combined with aqueous potassium carbonate solution and extracted twice with ethyl acetate. The combined organic phases were dried over $Na_2SO_4$ and evaporated down. The residue was crystallised from ether.

Yield: 8.3 g of a compound X5f (colourless solid)

8.2 g of the compound X5f were placed in 100 mL dimethylformamide, combined with 2.8 mL (45 mmol) methyl iodide and at −10° C. 1.8 g (45 mmol) sodium hydride was added batchwise as a 60% dispersion in mineral oil. The reaction mixture was stirred for 30 minutes at 0° C., poured onto 400 mL ice water and the aqueous phase was extracted twice with ethyl acetate. The combined organic phases were dried over $Na_2SO_4$ and evaporated down. The residue was taken up in acetone/ether and the product was crystallised with ethereal hydrochloric acid solution.

Yield: 9.1 g of a compound X6f (colourless solid)

A suspension of 1.3 g of the compound X6f and 1.7 g (10 mmol) ethyl 4-aminobenzoate X7a in 15 mL toluene was combined with 0.4 g (0.6 mmol) 2,2'-bis-(diphenylphosphino)-1,1'-binaphthyl, 2.5 g (2.7 mmol) tris(dibenzylideneacetone)-dipalladium(0) and 1.5 g (5 mmol) caesium carbonate and stirred for 24 hours at 100° C. The reaction mixture was combined with 50 mL ethyl acetate and the precipitate formed was filtered off. The filtrate was evaporated down and purified by column chromatography (eluant: dichloromethane/methanol 9:1). The product was taken up in acetone and precipitated as the hydrochloride using ethereal hydrochloric acid solution.

Yield: 1.6 g of a compound X8f (yellow solid)

1.6 g of the compound X8f were suspended in 60 mL 1N aqueous hydrochloric acid and refluxed for 24 hours. After cooling the precipitate formed was suction filtered and washed with water and acetone.

Yield: 1.4 g of a compound X9f (colourless solid)

Intermediate Compound 7:

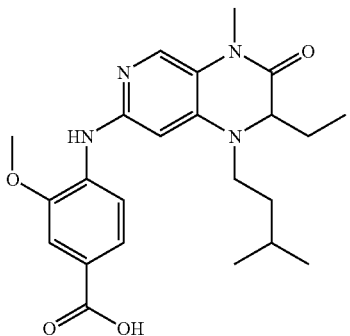

X9g

A suspension of 3.4 g of the compound X6f and 4.4 g (24 mmol) methyl 4-amino-3-methoxybenzoate X7b in 60 mL toluene was combined with 0.9 g (1.5 mmol) 2,2'-bis-(diphenylphosphino)-1,1'-binaphthyl, 0.9 g (1 mmol) tris(dibenzylideneacetone)-dipalladium(0) and 10 g (30 mmol) caesium carbonate and heated to 100° C. for 24 hours. After cooling the solid formed was suction filtered and the filtrate was evaporated down. The residue remaining was purified by column chromatography (eluant: cyclohexane/ethyl acetate 3:1).

Yield: 4.6 g of a compound X8g (brown solid)

4.4 g of the compound X8g were suspended in 60 mL 2N aqueous hydrochloric acid and refluxed for 18 hours. After cooling the precipitate formed was suction filtered and washed with acetone and ether.

Yield: 3.9 g of a compound X9g (colourless solid)

Intermediate Compound 8:

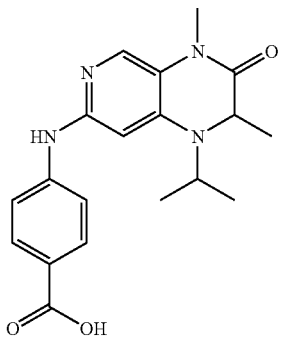

X9h 20.7 g of the compound X3d were placed in 150 mL acetonitrile, combined with 59.6 mL (0.7 mol) isopropylamine and stirred for 24 hours at ambient temperature. The reaction mixture was evaporated down, taken up in water and extracted with dichloromethane. The combined organic phases were dried over $Na_2SO_4$ and evaporated down. The oil obtained was taken up in ether and a little ethyl acetate and the product was crystallised by the addition of ethereal hydrochloric acid solution.

Yield: 20.5 g of a compound X4h (colourless solid)

A mixture of 9.1 g of the compound X4h and 15 g (0.11 mol) N-ethyldiisopropylamine in 50 mL dimethylformamide was refluxed for 7 days and then evaporated down. The residue was taken up in aqueous potassium carbonate solution and extracted with ethyl acetate. The combined organic phases were dried over $Na_2SO_4$, evaporated down and the residue was crystallised with ether.

Yield: 5.5 g of a compound X5h (light yellow solid)

18.2 g of the compound X5h were placed in 250 mL dimethylformamide and combined with 8.2 mL (0.13 mol) methyl iodide. The mixture was cooled to −5° C. and 4.0 g (0.10 mol) sodium hydride was added batchwise as a 60% dispersion in mineral oil. The reaction mixture was stirred for two hours at 0° C. and then poured onto 800 mL ice water. The precipitate formed was filtered off and was washed with water and petroleum ether.

Yield: 15.9 g of a compound X6h (light yellow solid)

A suspension of 1 g of the compound X6h and 1.4 g (10 mmol) ethyl 4-aminobenzoate X7a in 60 mL toluene was combined with 0.2 g (0.3 mmol) 2,2'-bis-(diphenylphosphino)-1,1'-binaphthyl, 0.3 g (0.3 mmol) tris(dibenzylideneacetone)-dipalladium(0) and 3.3 g (10 mmol) caesium carbonate and stirred for 65 hours at 100° C. The reaction mixture was filtered through cellulose, evaporated down and the residue was purified by column chromatography (eluant: ethyl acetate/petroleum ether 2:1).

Yield: 1.2 g of a compound X8h (yellow foam)

1 g of the compound X8h were suspended in 15 mL water, combined with 15 mL semiconc. hydrochloric acid and refluxed for 2 hours. After cooling the precipitate formed was suction filtered and washed with water, acetone and ether.

Yield: 0.9 g of a compound X9h (colourless solid)

Intermediate Compound 9:

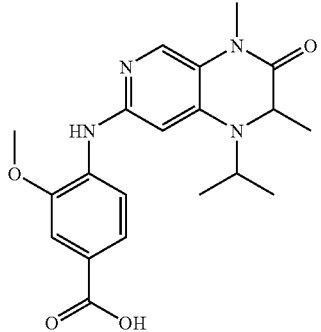

X9i

A suspension of 2.9 g of the compound X6h and 4.4 g (23 mmol) ethyl 4-amino-3-methoxybenzoate X7c in 120 mL toluene was combined with 0.8 g (1.3 mmol) 2,2'-bis-(diphenylphosphino)-1,1'-binaphthyl, 1 g (1.1 mmol) tris(dibenzylideneacetone)-dipalladium(0) and 10 g (30 mmol) caesium carbonate and heated to 100° C. for 72 hours. After cooling was the reaction mixture was filtered through cellulose and the filtrate was evaporated down. The residue remaining was purified by column chromatography (eluant: petroleum ether/ethyl acetate 1:2).

Yield: 3.6 g of a compound X8i (light brown solid)

3.6 g of the compound X8i were suspended in 20 mL water, combined with 15 mL semiconc. hydrochloric acid and refluxed for 2 hours. After cooling the precipitate formed was suction filtered and washed with water, acetone and ether.

Yield: 2.95 g of a compound X9i (colourless solid)

Intermediate Compound 10:

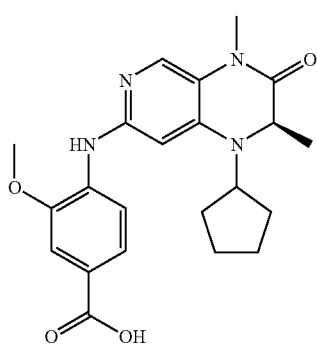

X9j 10 g (154 mmol) sodium azide were dissolved in 45 mL water and combined at 0° C. with 75 mL dichloromethane and 9.3 mL (55 mmol) trifluoromethanesulphonic acid anhydride. The reaction mixture was stirred for two hours and then extracted twice with 40 mL dichloromethane. The combined organic phases were washed with saturated aqueous sodium hydrogen carbonate solution and dried over $Na_2SO_4$. The solution thus obtained was added to a mixture of 2.5 g (28 mmol) D-alanine, 5.9 g (42 mmol) potassium carbonate and 70 mg (0.3 mmol) copper-(II)sulphate-pentahydrate in 90 mL water and 180 mL methanol. It was stirred for 12 hours at ambient temperature and then the organic solvent was eliminated in vacuo. The residue was diluted with water and adjusted to pH 6.2. Then it was extracted with ethyl acetate. The aqueous phase was then adjusted to pH 2 and the mixture was again extracted with ethyl acetate. These organic phases were dried over $Na_2SO_4$ and evaporated down.

Yield: 4.0 g of a compound X13a (light yellow oil)

3.3 g of the compound X13a were dissolved in 30 mL dichloromethane, combined with 5 mL (68 mmol) thionyl chloride and stirred for two hours at 50° C. The mixture was concentrated by rotary evaporation and the residue was combined with a solution of 6.6 g (28 mmol) 4,6-dichloro-pyridin-3-yl-amine dihydrochloride and 10 mL (124 mmol) pyridine in 10 mL dichloromethane. After 12 hours the mixture was combined with water and extracted with dichloromethane. The combined organic phases were dried over $Na_2SO_4$, evaporated down and purified by column chromatography (eluant: dichloromethane/methanol 100:5).

Yield: 4.9 g of a compound X11a (light brown solid)

In an argon atmosphere 7.1 g of the compound X11a were placed in 150 mL THF and 35 mL of a 1 M solution of trimethylphosphine in THF was added dropwise. The mixture was stirred overnight, then combined with water and evaporated down. The residue was taken up in water and extracted with dichloromethane. The combined organic phases were dried over $Na_2SO_4$ and evaporated down. The yellow oil obtained was taken up in acetone/ether and the product was crystallised by the addition of ethereal hydrochloric acid solution.

Yield: 5.4 g of a compound X12a (colourless solid)

6.3 g of the compound X12a were placed in 250 mL dichloromethane and combined with 2.2 g (26 mmol) cyclopentanone, 14 g (66 mmol) sodium triacetoxyborohydride and 3.3 g (40 mmol) sodium acetate. The mixture was stirred for 12 hours and then combined with aqueous sodium hydrogen carbonate solution. The organic phase was dried over $Na_2SO_4$ and evaporated down. The oil obtained was purified by column chromatography (eluant dichloromethane/methanol 100:2).

Yield: 5.5 of a compound X4j (light yellow oil)

A mixture of 1 g of the compound X4j and 3.5 mL (20 mmol) N-ethyldiisopropylamine in 5 mL dimethylformamide was heated to 150° C. for 34 hours. The reaction mixture was combined with water and extracted with dichloromethane. The combined organic phases were dried over $Na_2SO_4$ and evaporated down.

Yield: 0.7 g of a compound X5j (beige solid)

4.1 g of the compound X5j were placed in 10 mL dimethylformamide and combined with 1 mL (17 mmol) methyl iodide. At −5° C. 1.2 g (30 mmol) sodium hydride was added batchwise as a 60% dispersion in mineral oil. The reaction mixture was stirred for two hours at 0° C., combined with water and extracted with dichloromethane. The combined organic phases were dried over $Na_2SO_4$ and evaporated down.

Yield: 4.0 g of a compound X6j (orange oil)

A suspension of 4 g of the compound X6j and 2.8 g (15 mmol) methyl 4-amino-3-methoxybenzoate X7b in 70 mL toluene was combined with 0.6 g (0.9 mmol) 2,2'-bis-(diphenylphosphino)-1,1'-binaphthyl, 0.9 g (0.9 mmol) tris(dibenzylideneacetone)-dipalladium(0) and 12 g (37 mmol) caesium carbonate and refluxed for 50 hours. After cooling the reaction mixture was filtered through cellulose and the filtrate was evaporated down. The residue remaining was taken up in ethyl acetate, washed with water, dried over $Na_2SO_4$, filtered through activated charcoal and evaporated down. The product was purified by column chromatography (eluant: dichloromethane/methanol 95:5).

Yield: 3.1 g of a compound X8j (red oil)

3.1 g of the compound X8j were suspended in 30 mL water, combined with 15 mL conc. hydrochloric acid and refluxed for 10 hours. After cooling the precipitate formed was suction filtered and washed with water, acetone and ether.

Yield: 2.2 g of a compound X9j (colourless solid)

Synthesis of selected Examples from Table 1

EXAMPLE 2

0.1 g of the compound X9d, 0.08 g TBTU and 1 mL DIPEA were dissolved in 2 mL dimethylformamide and stirred for 10 minutes at 25° C. Then 0.05 g of 3-picolylamine were added and the mixture was stirred for a further 15 minutes at 70° C. The reaction mixture was evaporated down, combined with 10 mL ethyl acetate and washed with water. The aqueous phase was extracted with ethyl acetate. The combined organic phases were washed with water, dried over $Na_2SO_4$ and evaporated down. The residue was crystallised from ethyl acetate.

Yield: 0.067 g (colourless solid) m.p. 167-168° C.

EXAMPLE 5

0.06 g of the compound X9e, 0.055 g TBTU and 0.5 g DIPEA were dissolved in 2 mL dimethylformamide and stirred for 10 minutes at 25° C. Then 0.05 g of 4-picolylamine were added and the mixture was stirred for a further 30 minutes at 25° C. The reaction mixture was evaporated down and combined with 20 mL ethyl acetate and 10 mL water. The aqueous phase was extracted with ethyl acetate. The combined organic phases were washed with water, dried over $Na_2SO_4$ and evaporated down. The residue was purified by column chromatography (eluant: dichloromethane/ethyl acetate/methanol 70:20:10).

Yield: 0.043 g (colourless solid)

EXAMPLE 6

0.23 g of the compound X9g, 0.18 g TBTU and 0.29 mL DIPEA were dissolved in 5 mL dimethylformamide and stirred for 10 minutes at 25° C. Then 0.07 g 3-picolylamine were added and the mixture was stirred for a further 15 minutes at 25° C. The reaction mixture was evaporated down and combined with 20 mL ethyl acetate and 10 mL water. The aqueous phase was extracted with ethyl acetate. The combined organic phases were washed with water, dried over $Na_2SO_4$ and evaporated down. The residue was purified by column chromatography (eluant: dichloromethane/ethyl acetate/methanol 70:20:10) and precipitated as the hydrochloride from ethyl acetate.

Yield: 0.16 g (colourless solid) m.p. 104-112° C.

EXAMPLE 8

0.23 g of the compound X9g, 0.18 g TBTU and 0.30 mL DIPEA were dissolved in 5 mL dimethylformamide and stirred for 10 minutes at 25° C. Then 0.06 g cyclopropylamine were added and the mixture was stirred for a further 15 minutes at 25° C. The reaction mixture was evaporated down and combined with 20 mL ethyl acetate and 10 mL aqueous potassium carbonate solution. The aqueous phase was extracted with ethyl acetate. The combined organic phases were washed with water, dried over $Na_2SO_4$ and evaporated down. The residue was purified by column chromatography (eluant: dichloromethane/ethyl acetate/methanol 70:20:10) and crystallised from ethyl acetate. The solid obtained was washed with ether.

Yield: 0.12 g (colourless solid) m.p. 201-203° C.

EXAMPLE 13

0.15 g of the compound X9f, 0.15 g TBTU and 0.29 mL DIPEA were dissolved in 5 mL dichloromethane and stirred for 30 minutes at 25° C. Then 0.10 g cyclobutylamine were added and the mixture was stirred overnight at 25° C. The reaction mixture was evaporated down and the residue was combined with 20 mL water. The precipitate formed was suction filtered, taken up in dichloromethane and this solution was dried over $Na_2SO_4$ and evaporated down. The product was crystallised from acetone by the addition of ethereal hydrochloric acid solution.

Yield: 0.13 g (colourless solid) m.p. 238-239° C.

EXAMPLE 18

A mixture of 0.3 g of the compound X9a and 0.3 g thionyl chloride in 30 mL dichloromethane was refluxed for 24 hours. The reaction mixture was evaporated down, taken up in 10 mL dichloromethane, combined with 0.5 g 3-aminopyridine and stirred for 30 minutes at 250° C. After evaporation the residue was diluted with water and the precipitate formed was suction filtered and washed with water. The solid was dissolved in dichloromethane, dried over $Na_2SO_4$ and evaporated down. The product was crystallised by the addition of acetone.

Yield: 0.09 g (colourless solid) m.p. 231-232° C.

EXAMPLE 22

0.1 g of the compound X9b, 0.09 g TBTU and 0.30 mL DIPEA were dissolved in 5 mL dichloromethane and stirred for 20 minutes at 25° C. Then 0.04 g of 1-methyl-piperidin-4-ylamine were added and the mixture was stirred for a further 4 hours at 25° C. The solution was diluted with 15 mL dichloromethane and washed with water. The organic phase was evaporated down and the residue was precipitated by the addition of ether and ethyl acetate. The solid obtained was stirred with methanol/ether and suction filtered.

Yield: 0.024 g (colourless solid)

EXAMPLE 25

0.1 g of the compound X9c, 0.09 g TBTU and 0.30 mL DIPEA were dissolved in 2 mL dimethylformamide and stirred for 20 minutes at 25° C. Then 0.04 g 4-aminopyridine were added and the mixture was stirred for a further 1.5 hours at 100° C. The solution was diluted with 15 mL dichloromethane and washed with water. The organic phase was evaporated down and the residue was purified by column chromatography (eluant: dichloromethane→dichloromethane/methanol 90:10). The product was precipitated by the addition of petroleum ether, ether and ethyl acetate.

Yield: 0.01 g (colourless solid) m.p. 117° C.

EXAMPLE 44

0.15 g of the compound X9i, 0.15 g TBTU and 0.10 mL DIPEA were dissolved in 1 mL dichloromethane and stirred for 30 minutes at 25° C. Then 0.07 g 8-methyl-8-aza-bicyclo [3.2.1]oct-3-ylamine were added and the mixture was stirred overnight at 25° C. The reaction mixture was washed with aqueous potassium carbonate solution and the organic phase was evaporated down.

The residue was by crystallised the addition of ether.

Yield: 0.16 g (colourless solid) m.p. >200° C.

EXAMPLE 45

0.15 g of the compound X9i, 0.14 g TBTU and 0.11 mL DIPEA were dissolved in 1 mL dichloromethane and stirred for 30 minutes at 25° C. Then 0.15 mL ammonia were added as a 7 N solution in methanol and the mixture was stirred overnight at 25° C. The reaction mixture was filtered off and the filtrate was washed with aqueous potassium carbonate solution. The organic phase was evaporated down and the residue was crystallised by the addition of ether.

Yield: 0.13 g (colourless solid) m.p. >200° C.

EXAMPLE 46

0.1 g of the compound X9h, 0.11 g TBTU and 0.07 mL DIPEA were dissolved in 1 mL dichloromethane and stirred for 30 minutes at 25° C. Then 0.03 g 3-aminopyridin were added and the mixture was stirred overnight at 25° C. The reaction mixture was washed with aqueous potassium carbonate solution and the organic phase was evaporated down. The residue was purified by column chromatography (eluant: dichloromethane/methanol 100:5 to 100:7) and the product was crystallised by the addition of ether.

Yield: 0.04 g (yellowish solid) m.p. >200° C.

EXAMPLE 49

0.1 g of the compound X9j, 0.09 g TBTU and 0.25 mL DIPEA were dissolved in 1.5 mL dichloromethane and stirred for 30 minutes at 250° C. Then 0.02 mL isopropylamine were added and the mixture was stirred overnight at 25° C. The reaction mixture was washed with aqueous potassium carbonate solution and the organic phase was evaporated down. The residue was taken up in acetone/ether and the product was precipitated by the addition of ethereal hydrochloric acid solution.

Yield: 0.07 g (colourless solid) m.p. 179-181° C.

EXAMPLE 51

0.1 g of the compound X9j, 0.09 g TBTU and 0.50 mL DIPEA were dissolved in 1.5 mL dichloromethane and stirred for 30 minutes at 25° C. Then 0.07 g trans-4-morpholino-cyclohexylamine were added and the mixture was stirred overnight at 25° C. The reaction mixture was washed with aqueous potassium carbonate solution and the organic phase was evaporated down. The residue was crystallised by the addition of ether.

Yield: 0.08 g (light yellow solid) m.p. 166-168° C.

EXAMPLE 52

0.1 g of the compound X9j, 0.09 g TBTU and 0.25 mL DIPEA were dissolved in 1.5 mL dichloromethane and stirred for 30 minutes at 25° C. Then 0.03 g of 1-methylpiperidin-4-amine were added and the mixture was stirred overnight at 25° C. The reaction mixture was washed with aqueous potassium carbonate solution and the organic phase was evaporated down. The residue was crystallised by the addition of ether.

Yield: 0.03 g (light yellow solid) m.p. 148-151° C.

trans-4-morpholino-cyclohexylamine

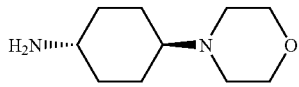

dibenzyl-4-morpholino-cyclohexylamine 3.9 g (30 mmol) ) 4-dibenzylcyclohexanone were dissolved in 100 mL CH$_2$Cl$_2$ and the mixture was stirred with 3.9 g (45 mmol) morpholine and 9.5 g (45 mmol) NaBH(OAc)$_3$ for 12 hours at 25° C. Then water and potassium carbonate were added, the organic phase was separated off, dried [and] evaporated down. The residue was purified on a silica gel column (eluant: ethyl acetate 90/methanol 10+1% conc. ammonia). The appropriate fractions were evaporated down in vacuo.

Yield: 6.6 g (60%) cis-isomer and 2 g (18%) trans-isomer.

Alternatively, trans-dibenzyl-4-morpholino-cyclohexylamine may be prepared by the following method:

33 g (112 mmol) 4-dibenzylcyclohexanon were dissolved in 300 mL methanol, combined with 17.4 g (250 mmol) hydroxylaminehydrochlorid and stirred for 4 hours at 60° C. The solvent was evaporated down in vacuo, combined with 500 mL water and 50 g potassium carbonate and extracted twice with 300 mL dichloromethane. The organic phases were dried, evaporated down in vacuo, the residue was crystallised from petroleum ether, dissolved in 1.5 L ethanol and heated to 70° C. 166 g of sodium was added batchwise and refluxed until the sodium dissolved. The solvent was removed, the residue was combined with 100 mL water and extracted twice with 400 mL ether. The organic phases were washed with water, dried, evaporated down in vacuo and the trans-isomer was isolated through a column (eluant: ethyl acetate 80/methanol 20+2% conc. ammonia).

Yield: 12.6 g (41%).

6.8 g (23 mmol) trans-1-amino-4-dibenzylaminocyclohexane was dissolved in 90 mL DMF and stirred with 5 mL (42 mmol) 2,2'-dichloroethylether and 5 g potassium carbonate for 8 hours at 100° C. After cooling, 30 mL water was added, the precipitated crystals were suction filtered and purified through a short column (eluant: ethyl acetate). The residue was crystallised from methanol and conc. hydrochloric acid as the dihydrochloride.

Yield: 7.3 g (72%).

trans-4-morpholino-cyclohexylamine 7.2 g (16.4 mmol) trans-dibenzyl-4-morpholino-cyclohexylamine were dissolved in 100 mL methanol and hydrogenated on 1.4 g Pd/C (10%) at 30-50° C. The solvent was eliminated in vacuo and the residue was crystallised from ethanol and conc. hydrochloric acid.

Yield: 3.9 g (93%); m.p. 312 ° C.

The compounds of formula (I) listed in Table 1, for example, were obtained analogously to the method described hereinbefore.

TABLE 1

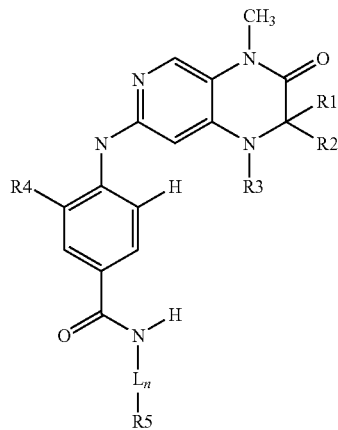

| Example | Config R1/R2 | R1 | R2 | R3 | R4 | L$_n$—R5 | melting point |
|---|---|---|---|---|---|---|---|
| 1 | rac | H | *—CH$_3$ | *—CH$_2$CH(CH$_3$)CH$_3$ (branched) | H | *—CH$_2$-phenyl | 227-228° C. decomposition |

TABLE 1-continued

| Example | Config R1/R2 | R1 | R2 | R3 | R4 | L$_n$—R5 | melting point |
|---|---|---|---|---|---|---|---|
| 2 | rac | H | *—CH$_3$ | *—CH$_2$CH$_2$CH(CH$_3$)$_2$ | H | *—O—CH$_3$ | 167-168° C. decomposition |
| 3 | rac | H | *—CH$_3$ | *—CH$_2$CH$_2$CH(CH$_3$)$_2$ | H | *—CH$_2$-(4-pyridyl) | 179-180° C. decomposition |
| 4 | rac | H | *—CH$_3$ | *—CH$_2$CH$_2$CH(CH$_3$)$_2$ | *—O—CH$_3$ | *—CH$_2$-(3-pyridyl) | 97-98° C. decomposition |
| 5 | rac | H | *—CH$_3$ | *—CH$_2$CH(CH$_3$)CH$_2$CH$_3$ | *—O—CH$_3$ | *—CH$_2$-(4-pyridyl) | |
| 6 | rac | H | *—CH$_2$CH$_3$ | *—CH$_2$CH$_2$CH(CH$_3$)$_2$ | *—O—CH$_3$ | *—CH$_2$-(3-pyridyl) | 104-112° C. |
| 7 | rac | H | *—CH$_2$CH$_3$ | *—CH$_2$CH$_2$CH(CH$_3$)$_2$ | *—O—CH$_3$ | *—CH$_2$-(4-pyridyl) | 202-205° C. |

TABLE 1-continued

| Example | Config R1/R2 | R1 | R2 | R3 | R4 | L$_n$—R5 | melting point |
|---------|--------------|----|----|----|----|----------|---------------|
| 8 | rac | H | *—CH$_2$CH$_3$ | *—CH$_2$CH$_2$CH(CH$_3$)$_2$ | *—OCH$_3$ | *-cyclopropyl | 201-203° C. |
| 9 | rac | H | *—CH$_2$CH$_3$ | *—CH$_2$CH$_2$CH(CH$_3$)$_2$ | *—OCH$_3$ | H | 259-260° C. |
| 10 | rac | H | *—CH$_2$CH$_3$ | *—CH$_2$CH$_2$CH(CH$_3$)$_2$ | *—OCH$_3$ | *-pyridin-3-yl | |
| 11 | rac | H | *—CH$_2$CH$_3$ | *—CH$_2$CH(CH$_3$)CH$_2$CH$_3$ | *—OCH$_3$ | *-pyridin-4-yl | |
| 12 | rac | H | *—CH$_2$CH$_3$ | *—CH$_2$CH$_2$CH(CH$_3$)$_2$ | H | *-cyclopropyl | 209-210° C. |
| 13 | rac | H | *—CH$_2$CH$_3$ | *—CH$_2$CH$_2$CH(CH$_3$)$_2$ | H | *-cyclobutyl | 238-239° C. |

TABLE 1-continued
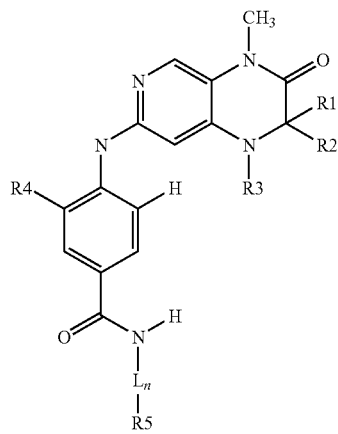
| Example | Config R1/R2 | R1 | R2 | R3 | R4 | L$_n$—R5 | melting point |
|---|---|---|---|---|---|---|---|
| 14 | rac | H | *\_CH₃ | *\_(CH₂)₂CH(CH₃)₂ | H | *\_CH(CH₃)₂ | 259-260° C. |
| 15 | rac | H | *\_CH₃ | *\_(CH₂)₂CH(CH₃)₂ | H | *\_CH₃ | 236-237° C. |
| 16 | rac | H | *\_CH₃ | *\_(CH₂)₂CH(CH₃)₂ | H | *-pyridin-3-yl | 146-147° C. decomposition |
| 17 | rac | H | *\_CH₃ | *\_CH₂CH(CH₃)₂ | H | *-pyridin-4-yl | 240-241° C. decomposition |
| 18 |  | H | H | *\_(CH₂)₂CH(CH₃)₂ | H | *-pyridin-3-yl | 231-232° C. decomposition |
| 19 |  | *\_CH₃ | *\_CH₃ | *\_(CH₂)₂CH(CH₃)₂ | H | *\_CH(CH₃)₂ | 152° C. |

TABLE 1-continued

| Example | Config R1/R2 | R1 | R2 | R3 | R4 | L$_n$—R5 | melting point |
|---|---|---|---|---|---|---|---|
| 20 | | *—CH$_3$ | *—CH$_3$ | *-CH$_2$CH$_2$CH(CH$_3$)$_2$ | H | *-cyclopropyl | 222° C. |
| 21 | | *—CH$_3$ | *—CH$_3$ | *-CH$_2$CH$_2$CH(CH$_3$)$_2$ | H | H | 150° C. |
| 22 | | *—CH$_3$ | *—CH$_3$ | *-CH$_2$CH$_2$CH(CH$_3$)$_2$ | H | *-(1-methylpiperidin-4-yl) | |
| 23 | | *—CH$_3$ | *—CH$_3$ | *-CH$_2$CH$_2$CH(CH$_3$)$_2$ | H | *-(pyridin-4-yl) | 167° C. |
| 24 | | *—CH$_3$ | *—CH$_3$ | *-CH$_2$CH$_2$CH(CH$_3$)$_2$ | H | *-(pyridin-3-yl) | 135° C. |
| 25 | | *—CH$_3$ | *—CH$_3$ | *-CH$_2$CH$_2$CH(CH$_3$)$_2$ | *-OCH$_3$ | *-(pyridin-4-yl) | 117° C. |

TABLE 1-continued
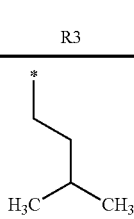
| Example | Config R1/R2 | R1 | R2 | R3 | R4 | Lₙ—R5 | melting point |
|---|---|---|---|---|---|---|---|
| 26 | | *CH₃ | *CH₃ | *CH(CH₂)CH(CH₃)₂ | *OCH₃ | *-(4-(1-methylpiperidinyl)) | 165° C. |
| 27 | | *CH₃ | *CH₃ | *CH(CH₂)CH(CH₃)₂ | *OCH₃ | *CH(CH₃)₂ | 109° C. |
| 28 | | *CH₃ | *CH₃ | *CH(CH₂)CH(CH₃)₂ | *OCH₃ | H | 220° C. |
| 29 | | *CH₃ | *CH₃ | *CH(CH₂)CH(CH₃)₂ | *OCH₃ | *-(3-pyridyl) | — |
| 30 | rac | H | *CH₃ | *CH₂CH(CH₃)₂ | H | *-cyclopropyl | 160° C. |
| 31 | rac | H | *CH₃ | *CH₂CH(CH₃)₂ | H | *-(4-(1-methylpiperidinyl)) | 186-187° C. |
| 32 | rac | H | *CH₃ | *CH₂CH(CH₃)₂ | H | *CH₃ | 206-207° C. |

TABLE 1-continued

[Core structure: 1-methyl-2-oxo-pyrido[3,4-b]pyrazine with R1, R2 at position 3, R3 on ring N, linked via NH to a benzene ring bearing R4 and a carboxamide —C(=O)NH—L$_n$—R5]

| Example | Config R1/R2 | R1 | R2 | R3 | R4 | L$_n$—R5 | melting point |
|---|---|---|---|---|---|---|---|
| 33 | rac | H | *—CH$_3$ | *—CH$_2$—CH(CH$_3$)$_2$ (isobutyl) | H | *—CH$_2$—CH(CH$_3$)$_2$ (isobutyl) | 210-211° C. |
| 34 | rac | H | *—CH$_3$ | *—CH$_2$—CH(CH$_3$)$_2$ (isobutyl) | H | H | |
| 35 | rac | H | *—CH$_3$ | *—CH$_2$—CH(CH$_3$)$_2$ (isobutyl) | H | *-cyclobutyl | |
| 36 | rac | H | *—CH$_3$ | *—CH$_2$—CH(CH$_3$)$_2$ (isobutyl) | H | *-(N-methyl-8-azabicyclo[3.2.1]octyl) | >250° C. |
| 37 | | *—CH$_3$ | *—CH$_3$ | *—CH$_2$CH$_2$CH(CH$_3$)$_2$ | *—OCH$_3$ | *-cyclopropyl | 187° C. |
| 38 | | *—CH$_3$ | *—CH$_3$ | *—CH$_2$CH$_2$CH(CH$_3$)$_2$ | *—OCH$_3$ | *-(N-methyl-azabicyclic) | 144° C. |
| 39 | rac | H | *—CH$_3$ | *—CH$_2$CH(CH$_3$)$_2$ | *—CH$_2$—OCH$_3$ | *—CH$_3$ | 162-163° C. |

TABLE 1-continued

| Example | Config R1/R2 | R1 | R2 | R3 | R4 | L$_n$—R5 | melting point |
|---|---|---|---|---|---|---|---|
| 40 | rac | H | *—CH$_3$ | *—CH$_2$CH(CH$_3$)$_2$ | *—OCH(CH$_3$)$_2$ | *—CH(CH$_3$)$_2$ | 188-189° C. |
| 41 | rac | H | *—CH$_3$ | *—CH$_2$CH(CH$_3$)$_2$ | *—OCH$_3$ | *-cyclopropyl | 201-203° C. |
| 42 | rac | H | *—CH$_3$ | *—CH$_2$CH(CH$_3$)$_2$ | *—OCH$_3$ | *-cyclobutyl | 191-192° C. |
| 43 | rac | H | *—CH$_3$ | *—CH$_2$CH(CH$_3$)$_2$ | *—OCH$_3$ | *-(1-methylpiperidin-4-yl) | 160-161° C. |
| 44 | rac | H | *—CH$_3$ | *—CH$_2$CH(CH$_3$)$_2$ | *—OCH$_3$ | *-(1-methyl-8-azabicyclo) | >200° C. |
| 45 | rac | H | *—CH$_3$ | *—CH$_2$CH(CH$_3$)$_2$ | *—OCH$_3$ | H | >200° C. |
| 46 | rac | H | *—CH$_3$ | *—CH(CH$_3$)$_2$ | H | *-(pyridin-3-yl) | >200° C. |

TABLE 1-continued
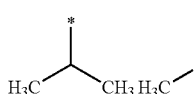
| Example | Config R1/R2 | R1 | R2 | R3 | R4 | L$_n$—R5 | melting point |
|---|---|---|---|---|---|---|---|
| 47 | rac | H | *—CH$_3$ | *CH(CH$_3$)$_2$CH$_2$— | *—O—CH$_3$ | *-pyridin-3-yl | |
| 48 | R | H | *—CH$_3$ | *-cyclopentyl | *—O—CH$_3$ | *-cyclopropyl | |
| 49 | R | H | *—CH$_3$ | *-cyclopentyl | *—O—CH$_3$ | *—CH(CH$_3$)$_2$ | 179-181° C. |
| 50 | R | H | *—CH$_3$ | *-cyclopentyl | *—O—CH$_3$ | *-(4-(4-methylpiperazin-1-yl)phenyl) | |
| 51 | R | H | *—CH$_3$ | *-cyclopentyl | *—O—CH$_3$ | *-(trans-4-morpholinocyclohexyl) | 166-168° C. |

TABLE 1-continued

| Example | Config R1/R2 | R1 | R2 | R3 | R4 | L$_n$—R5 | melting point |
|---|---|---|---|---|---|---|---|
| 52 | R | H | *—CH₃ | *-cyclopentyl | *-OCH₃ | *-(N-methylpiperidin-4-yl) | 148-151° C. |
| 53 | R | H | *—CH₃ | *-cyclopentyl | *-OCH₃ | H | 140-142° C. |
| 54 | R | H | *—CH₃ | *-cyclopentyl | *-OCH₃ | *—CH₃ | 179-181° C. |
| 55 | R | H | *—CH₃ | *-cyclopentyl | *-OCH₃ | *-(pyridin-3-yl) | — |

As has been found, the compounds of general formula (I) are characterised by their wide range of applications in the therapeutic field. Particular mention should be made of those applications in which the inhibition of specific cell cycle kinases, particularly the inhibiting effect on the proliferation of cultivated human tumour cells but also the proliferation of other cells, such as endothelial cells, for example, plays a part.

As could be demonstrated by DNA staining followed by FACS analysis, the inhibition of proliferation brought about by the compounds according to the invention is mediated by the arrest of the cells, particularly at the G2/M phase of the cell cycle. The cells arrest, depending on the cells used, for a specific length of time in this phase of the cell cycle before programmed cell death is initiated. An arrest in the G2/M phase of the cell cycle is triggered, for example, by the inhibition of specific cell cycle kinases. In view of their biological properties the compounds of general formula I according to the invention, their isomers and their physiologically acceptable salts are suitable for the treatment of diseases characterised by excessive or abnormal cell proliferation.

Such diseases include, for example: viral infections (e.g. HIV and Kaposi's sarcoma); inflammatory and autoimmune diseases (e.g. colitis, arthritis, Alzheimer's disease, glomerulonephritis and wound healing); bacterial, fungal and/or parasitic infections; leukaemias, lymphoma and solid tumours; skin diseases (e.g. psoriasis); bone diseases; cardiovascular diseases (e.g. restenosis and hypertrophy). They are also suitable for protecting proliferating cells (e.g. hair, intestinal, blood and progenitor cells) from damage to their DNA caused by radiation, UV treatment and/or cytostatic treatment (Davis et al., 2001).

The new compounds may be used for the prevention, short-term or long-term treatment of the abovementioned diseases, also in combination with other active substances used for the same indications, e.g. cytostatics, hormones or antibodies.

The activity of the compounds according to the invention was determined in the PLK1 inhibition assay, in the cytotoxicity test on cultivated human tumour cells and/or in a FACS analysis, for example on HeLaS3 cells. In both test methods, the compounds exhibited a good to very good activity, i.e. for example an $EC_{50}$ value in the HeLaS3 cytotoxicity test of less than 5 μmol/L, generally less than 1 μmol/L and an $IC_{50}$ value in the PLK1 inhibition assay of less than 1 μmol/L.

PLK1 Kinase Assay

Preparation of Enzyme:

Recombinant human PLK1 enzyme attached to GST at its N-terminal end is isolated from Baculovirus-infected insect cells (Sf21). Purification is carried out by affinity chromatography on glutathione sepharose columns.

$4 \times 10^7$ Sf21 cells (*Spodoptera frugiperda*) in 200 ml of Sf-900 II Serum free insect cell medium (Life Technologies) are seeded in a spinner flask. After 72 hours' incubation at 27° C. and 70 rpm, $1 \times 10^8$ Sf21 cells are seeded in a total of 180 ml medium in a new spinner flask. After another 24 hours, 20 ml of recombinant Baculovirus stock suspension are added and the cells are cultivated for 72 hours at 27° C. at 70 rpm. 3 hours before harvesting, okadaic acid is added (Calbiochem, final concentration 0.1 μM) and the suspension is incubated further. The cell number is determined, the cells are removed by centrifuging (5 minutes, 4° C., 800 rpm) and washed 1× with PBS (8 g NaCl/l, 0.2 g KCl/l, 1.44 g $Na_2HPO_4$/l, 0.24 g $KH_2PO4$/l). After centrifuging again the pellet is flash-frozen in liquid nitrogen. Then the pellet is quickly thawed and resuspended in ice-cold lysing buffer (50 mM HEPES pH 7.5, 10 mM $MgCl_2$, 1 mM DTT, 5 μg/ml leupeptin, 5 μg/ml aprotinin, 100 μM NaF, 100 μM PMSF, 10 mM β-glycerolphosphate, 0.1 mM $Na_3VO_4$, 30 mM 4-nitrophenylphosphate) to give $1 \times 10^8$ cells/17.5 ml. The cells are lysed for 30 minutes on ice. After removal of the cell debris by centrifugation (4000 rpm, 5 minutes) the clear supernatant is combined with glutathione sepharose beads (1 ml resuspended and washed beads per 50 ml of supernatant) and the mixture is incubated for 30 minutes at 4° C. on a rotating board. Then the beads are washed with lysing buffer and the recombinant protein is eluted from the beads with 1 ml eluting buffer/ml resuspended beads (eluting buffer: 100 mM Tris/HCl pH=8.0, 120 mM NaCl, 20 mM reduced glutathione (Sigma G-4251), 10 mM $MgCl_2$, 1 mM DTT). The protein concentration is determined by Bradford Assay.

Assay

The following components are combined in a well of a 96-well round-bottomed dish (Greiner bio-one, PS Microtitre plate No. 650101):

10 μl of the compound to be tested in variable concentrations (e.g. beginning at 300 μM, and dilution to 1:3) in 6% DMSO, 0.5 mg/ml casein (Sigma C-5890), 60 mM β-glycerophosphate, 25 mM MOPS pH=7.0, 5 mM EGTA, 15 mM $MgCl_2$, 1 mM DTT 20 μl substrate solution (25 mM MOPS pH=7.0, 15 mM $MgCl_2$, 1 mM DTT, 2.5 mM EGTA, 30 mM β-glycerophosphate, 0.25 mg/ml casein)

20 μl enzyme dilution (1:100 dilution of the enzyme stock in 25 mM MOPS pH=7.0, 15 mM $MgCl_2$, 1 mM DTT)

10 μl ATP solution (45 μM ATP with $1.11 \times 10^6$ Bq/ml gamma-P33-ATP).

The reaction is started by adding the ATP solution and continued for 45 minutes at 30° C. with gentle shaking (650 rpm on an IKA Schüttler MTS2). The reaction is stopped by the addition of 125 μl of ice-cold 5% TCA per well and incubated on ice for at least 30 minutes. The precipitate is transferred by harvesting onto filter plates (96-well microtitre filter plate: UniFilter-96, GF/B; Packard; No. 6005177), then washed four times with 1% TCA and dried at 60° C. After the addition of 35 μl scintillation solution (Ready-Safe; Beckmann) per well the plate is sealed shut with sealing tape and the amount of P33 precipitated is measured with the Wallac Betacounter.

The measured data are evaluated using the standard Graphpad software (Levenburg-Marquard Algorhythmus).

Measurement of Cytotoxicity on Cultivated Human Tumour Cells

To measure cytotoxicity on cultivated human tumour cells, cells of cervical carcinoma tumour cell line HeLa S3 (obtained from American Type Culture Collection (ATCC)) are cultivated in Ham's F12 Medium (Life Technologies) and 10% foetal calf serum (Life Technologies) and harvested in the log growth phase. Then the HeLa S3 cells are placed in 96-well plates (Costar) at a density of 1000 cells per well and incubated overnight in an incubator (at 37° C. and 5% CO2), while on each plate 6 wells are filled with medium alone (3 wells as the medium control, 3 wells for incubation with reduced AlamarBlue reagent). The active substances are added to the cells in various concentrations (dissolved in DMSO; DMSO final concentration: 0.1%) (in each case as a triple measurement). After 72 hours incubation 20 μl AlamarBlue reagent (AccuMed International) are added to each well, and the cells are incubated for a further 7 hours. As a control, 20 μl reduced AlamarBlue reagent is added to each of 3 wells (AlamarBlue reagent, which is autoclaved for 30 min). After 7 h incubation the colour change of the AlamarBlue reagent in the individual wells is determined in a Perkin Elmer fluorescence spectrophotometer (excitation 530 nm, emission 590 nm, slits 15, integrate time 0.1). The amount of AlamarBlue reagent reacted represents the metabolic activity of the cells. The relative cell activity is calculated as a percentage of the control (HeLa S3 cells without inhibitor) and the active substance concentration which inhibits the cell activity by 50% ($IC_{50}$) is derived. The values are calculated from the average of three individual measurements—with correction of the dummy value (medium control).

FACS Analysis

Propidium iodide (PI) binds stoichiometrically to double-stranded DNA, and is thus suitable for determining the proportion of cells in the G1, S, and G2/M phase of the cell cycle on the basis of the cellular DNA content. Cells in the G0 and G1 phase have a diploid DNA content (2N), whereas cells in the G2 or mitosis phase have a 4N DNA content.

For PI staining, for example, 0.4 million HeLa S3 cells were seeded onto a 75 $cm^2$ cell culture flask, and after 24 h either 0.1% DMSO was added as control or the substance was added in various concentrations (in 0.1% DMSO). The cells were incubated for 24 h with the substance or with DMSO before the cells were washed 2× with PBS and then detached with trypsin/EDTA. The cells were centrifuged (1000 rpm, 5 min, 4° C.), and the cell pellet was washed 2× with PBS before the cells were resuspended in 0.1 ml PBS. Then the cells were fixed with 80% ethanol for 16 hours at 4° C. or alternatively for 2 hours at −20° C. The fixed cells were centrifuged (1000 rpm, 5 min, 4° C.), washed with PBS and then centrifuged again. The cell pellet was resuspended in 2 ml 0.25% Triton X-100 in PBS, and incubated on ice for 5 min before 5 ml PBS are added and the mixture is centrifuged again. The cell pellet was resuspended in 350 μl PI staining solution (0.1 mg/ml RNase A (Sigma, No. R-4875), 10 μg/ml prodium iodide (Sigma, No. P-4864) in 1×PBS). The cells were incubated for 20 min in the dark with the staining buffer before being transferred into sample measuring containers for the FACS scan. The DNA measurement was carried out in a Becton Dickinson FACS Analyzer, with an argon laser (500 mW, emission 488 nm), and the DNA Cell Quest Programme (BD). The logarithmic PI fluorescence was determined with a band-pass filter (BP 585/42). The cell populations in the individual cell cycle phases were quantified using the ModFit LT Programme made by Becton Dickinson.

The compounds according to the invention were also tested accordingly on other tumour cells. For example, these compounds are effective on carcinomas of all kinds of tissue (e.g. breast (MCF7); colon (HCT116), head and neck (FaDu), lung (NCI-H460), pancreas (BxPC-3), prostate (DU145)), sarcomas (e.g. SK-UT-1B, Saos-2), leukaemias and lymphomas (e.g. HL-60, Jurkat, THP-1) and other tumours (e.g. melanomas (BRO), gliomas (U-87MG)) and could be used for such indications. This is evidence of the broad applicability of the compounds according to the invention for the treatment of all kinds of tumour types.

The compounds of general formula (I) may be used on their own or in conjunction with other active substances according to the invention, optionally also in conjunction with other pharmacologically active substances. Suitable preparations include for example tablets, capsules, suppositories, solutions,—particularly solutions for injection (s.c., i.v., i.m.) and infusion—elixirs, emulsions or dispersible powders. The content of the pharmaceutically active compound(s) should be in the range from 0.1 to 90 wt.-%, preferably 0.5 to 50 wt.-% of the composition as a whole, i.e. in amounts which are sufficient to achieve the dosage range specified below. The doses specified may, if necessary, be given several times a day.

Suitable tablets may be obtained, for example, by mixing the active substance(s) with known excipients, for example inert diluents such as calcium carbonate, calcium phosphate or lactose, disintegrants such as corn starch or alginic acid, binders such as starch or gelatine, lubricants such as magnesium stearate or talc and/or agents for delaying release, such as carboxymethyl cellulose, cellulose acetate phthalate, or polyvinyl acetate. The tablets may also comprise several layers.

Coated tablets may be prepared accordingly by coating cores produced analogously to the tablets with substances normally used for tablet coatings, for example collidone or shellac, gum arabic, talc, titanium dioxide or sugar. To achieve delayed release or prevent incompatibilities the core may also consist of a number of layers. Similarly the tablet coating may consist of a number or layers to achieve delayed release, possibly using the excipients mentioned above for the tablets.

Syrups or elixirs containing the active substances or combinations thereof according to the invention may additionally contain a sweetener such as saccharine, cyclamate, glycerol or sugar and a flavour enhancer, e.g. a flavouring such as vanillin or orange extract. They may also contain suspension adjuvants or thickeners such as sodium carboxymethyl cellulose, wetting agents such as, for example, condensation products of fatty alcohols with ethylene oxide, or preservatives such as p-hydroxybenzoates.

Solutions for injection and infusion are prepared in the usual way, e.g. with the addition of isotonic agents, preservatives such as p-hydroxybenzoates, or stabilisers such as alkali metal salts of ethylenediamine tetraacetic acid, optionally using emulsifiers and/or dispersants, whilst if water is used as the diluent, for example, organic solvents may optionally be used as solvating agents or dissolving aids, and transferred into injection vials or ampoules or infusion bottles.

Capsules containing one or more active substances or combinations of active substances may for example be prepared by mixing the active substances with inert carriers such as lactose or sorbitol and packing them into gelatine capsules.

Suitable suppositories may be made for example by mixing with carriers provided for this purpose, such as neutral fats or polyethyleneglycol or the derivatives thereof.

Excipients which may be used include, for example, water, pharmaceutically acceptable organic solvents such as paraffins (e.g. petroleum fractions), vegetable oils (e.g. groundnut or sesame oil), mono- or polyfunctional alcohols (e.g. ethanol or glycerol), carriers such as e.g. natural mineral powders (e.g. kaolins, clays, talc, chalk), synthetic mineral powders (e.g. highly dispersed silicic acid and silicates), sugars (e.g. cane sugar, lactose and glucose) emulsifiers (e.g. lignin, spent sulphite liquors, methylcellulose, starch and polyvinylpyrrolidone) and lubricants (e.g. magnesium stearate, talc, stearic acid and sodium lauryl sulphate).

The preparations are administered by the usual methods, preferably by oral or transdermal route, most preferably by oral route. For oral administration the tablets may, of course contain, apart from the abovementioned carriers, additives such as sodium citrate, calcium carbonate and dicalcium phosphate together with various additives such as starch, preferably potato starch, gelatine and the like. Moreover, lubricants such as magnesium stearate, sodium lauryl sulphate and talc may be used at the same time for the tabletting process. In the case of aqueous suspensions the active substances may be combined with various flavour enhancers or colourings in addition to the excipients mentioned above.

For parenteral use, solutions of the active substances with suitable liquid carriers may be used.

The dosage for intravenous use is from 1-1000 mg per hour, preferably between 5 and 500 mg per hour.

However, it may sometimes be necessary to depart from the amounts specified, depending on the body weight, the route of administration, the individual response to the drug, the nature of its formulation and the time or interval over which the drug is administered. Thus, in some cases it may be sufficient to use less than the minimum dose given above, whereas in other cases the upper limit may have to be exceeded. When administering large amounts it may be advisable to divide them up into a number of smaller doses spread over the day.

The formulation examples which follow illustrate the present invention without restricting its scope:

Examples of Pharmaceutical Formulations

| A) Tablets | per tablet |
|---|---|
| active substance | 100 mg |
| lactose | 140 mg |
| corn starch | 240 mg |
| polyvinylpyrrolidone | 15 mg |
| magnesium stearate | 5 mg |
| | 500 mg |

The finely ground active substance, lactose and some of the corn starch are mixed together. The mixture is screened, then moistened with a solution of polyvinylpyrrolidone in water, kneaded, wet-granulated and dried. The granules, the remaining corn starch and the magnesium stearate are screened and mixed together. The mixture is compressed to produce tablets of suitable shape and size.

| B) Tablets | per tablet |
|---|---|
| active substance | 80 mg |
| lactose | 55 mg |
| corn starch | 190 mg |
| microcrystalline cellulose | 35 mg |
| polyvinylpyrrolidone | 15 mg |
| sodium-carboxymethyl starch | 23 mg |
| magnesium stearate | 2 mg |
| | 400 mg |

The finely ground active substance, some of the corn starch, lactose, microcrystalline cellulose and polyvinylpyrrolidone are mixed together, the mixture is screened and worked with the remaining corn starch and water to form a granulate which is dried and screened. The sodiumcarboxymethyl starch and the magnesium stearate are added and mixed in and the mixture is compressed to form tablets of a suitable size.

| C) Ampoule solution | |
|---|---|
| active substance | 50 mg |
| sodium chloride | 50 mg |
| water for inj. | 5 ml |

The active substance is dissolved in water at its own pH or optionally at pH 5.5 to 6.5 and sodium chloride is added to make it isotonic. The solution obtained is filtered free from pyrogens and the filtrate is transferred under aseptic conditions into ampoules which are then sterilised and sealed by fusion. The ampoules contain 5 mg, 25 mg and 50 mg of active substance.

What is claimed is:

1. A Compound of the formula (I),

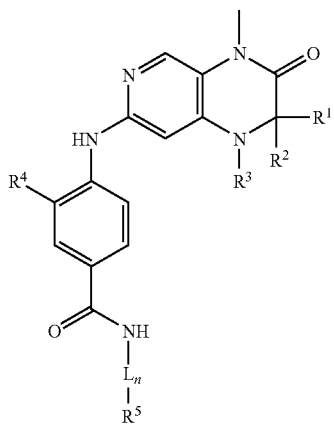

(I)

wherein
$R^1$, $R^2$ which may be identical or different denote hydrogen or a group selected from among $C_1$-$C_6$-alkyl, $C_2$-$C_6$-alkenyl and $C_2$-$C_6$-alkynyl, wherein each group may be optionally substituted by fluorine, or
$R^1$ and $R^2$ together denote a 2- to 5-membered alkyl bridge,
$R^3$ denotes hydrogen or a group selected from among $C_1$-$C_{12}$-alkyl optionally substituted by fluorine, $C_2$-$C_{12}$-alkenyl optionally substituted by fluorine, $C_2$-$C_{12}$-alkynyl optionally substituted by fluorine and $C_6$-$C_{14}$-aryl optionally substituted by one or more groups selected from OH, $NO_2$, CN, OMe, —$OCHF_2$, —$OCF_3$, —$NH_2$, halogen and $C_1$-$C_{10}$-alkyl, or
a group selected from among $C_3$-$C_{12}$-cycloalkyl optionally substituted by one or more groups selected from OH, $NO_2$, CN, OMe, —$OCHF_2$, —$OCF_3$, —$NH_2$, halogen, $C_1$-$C_{10}$-alkyl, —O—$C_1$-$C_3$-alkyl, —COOH, —COO—$C_1$-$C_4$-alkyl and —$CONH_2$, $C_3$-$C_{12}$-cycloalkenyl, $C_7$-$C_{12}$-polycycloalkyl, $C_7$-$C_{12}$-polycycloalkenyl and $C_5$-$C_{12}$-spirocycloalkyl,
$R^4$ denotes a group selected from among hydrogen, hydroxy and halogen, or
a group selected from among $C_1$-$C_3$-alkyl optionally substituted by fluorine, $C_2$-$C_6$-alkenyl optionally substituted by fluorine, $C_2$-$C_6$-alkynyl optionally substituted by fluorine, $C_1$-$C_5$-alkyloxy, $C_2$-$C_5$-alkenyloxy and $C_2$-$C_5$-alkynyloxy,
L denotes a linker selected from among $C_2$-$C_{10}$-alkyl optionally substituted by fluorine, $C_2$-$C_{10}$-alkenyl optionally substituted by fluorine, $C_6$-$C_{14}$-aryl optionally substituted by one or more groups selected from OH, $NO_2$, CN, OMe, —$OCHF_2$, —$OCF_3$, —$NH_2$, halogen and $C_1$-$C_{10}$-alkyl, —$C_1$-$C_4$-alkyl-$C_6$-$C_{14}$-aryl, $C_6$-$C_{14}$-heteroaryl wherein up to two C atoms are replaced by one or two nitrogen atoms, while these heteroaryl rings may optionally be anellated to a benzene ring and may optionally carry one or more substituents selected from F, Cl, Br, OH, OMe, methyl, ethyl, CN, $CONH_2$, $NH_2$, phenyl, pyridyl, and $C_3$-$C_{12}$-cycloalkyl optionally substituted by one or more groups selected from OH, $NO_2$, CN, OMe, —$OCHF_2$, —$OCF_3$, —$NH_2$, halogen, $C_1$-$C_{10}$-alkyl, —O—$C_1$-$C_3$-alkyl, —COOH, —COO—$C_1$-$C_4$-alkyl and —$CONH_2$,
n denotes 0 or 1,
$R^5$ denotes a group selected from among hydrogen or $C_1$-$C_6$-alkyl optionally substituted by fluorine, $C_1$-$C_6$-alkenyl optionally substituted by fluorine, $C_1$-$C_6$-alkynyl optionally substituted by fluorine, $C_3$-$C_{12}$-cycloalkyl optionally substituted by one or more groups selected from OH, $NO_2$, CN, OMe, —$OCHF_2$, —$OCF_3$, —$NH_2$, halogen, $C_1$-$C_{10}$-alkyl, —O—$C_1$-$C_3$-alkyl, —COOH, —COO—$C_1$-$C_4$-alkyl and —$CONH_2$, or
a group selected from among pyridyl, morpholinyl, piperidinyl, piperazinyl, piperazinylcarbonyl, pyrrolidinyl, tropenyl, sulphoxomorpholinyl, sulphonylmorpholinyl, thiomorpholinyl and azacycloheptyl,
optionally in the form of the tautomer, the racemate, the enantiomer, the diastereomer and the mixture thereof, or a pharmacologically acceptable acid addition salt thereof.

2. The Compound according to claim 1, wherein
$R^3$ to $R^5$, n and L are as hereinbefore defined, and
$R^1$, $R^2$ which may be identical or different denote hydrogen, or
a group selected from among methyl, ethyl, propyl, propargyl and allyl, or
$R^1$ and $R^2$ together represent cyclopropyl.

3. The Compound according to claim 2, wherein
$R^5$ denotes a group selected from among hydrogen or $C_1$-$C_6$-alkyl optionally substituted by fluorine, $C_3$-$C_{12}$-cycloalkyl optionally substituted by one or more groups selected from OH, $NO_2$, CN, OMe, —$OCHF_2$, —$OCF_3$, —$NH_2$, halogen, $C_1$-$C_{10}$-alkyl, —O—$C_1$-$C_3$-alkyl, —COOH, —COO—$C_1$-$C_4$-alkyl and —$CONH_2$, or a group selected from among pyridyl, morpholinyl, piperidinyl, piperazinyl and piperazinylcarbonyl.

4. The Compound according claim 3, wherein
$R^3$ denotes hydrogen, $C_1$-$C_6$-alkyl optionally substituted by fluorine, or $C_3$-$C_{12}$-cycloalkyl optionally substituted by one or more groups selected from OH, $NO_2$, CN, OMe, —$OCHF_2$, —$OCF_3$, —$NH_2$, halogen, $C_1$-$C_{10}$-alkyl, —O—$C_1$-$C_3$-alkyl, —COOH, —COO—$C_1$-$C_4$-alkyl and —$CONH_2$.

5. The Compound according claim 4, wherein
$R^4$ denotes a group selected from among hydrogen, hydroxy, halogen, methyl, ethyl, propynyloxy and methoxy.

6. A pharmaceutical composition comprising a compound according to claim 1 or a physiologically acceptable salt thereof, combined with conventional excipients and/or carriers.

7. A Process for preparing a compound of the formula (I) according to claim 1,

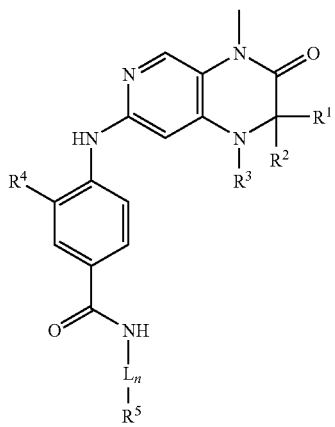

wherein
$R^1$-$R^5$, n and L have the meanings given in claim 1, comprising:
reacting a compound of the formula (II) under suitable conditions

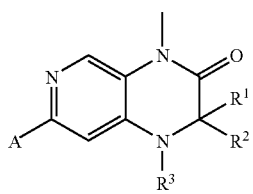
(II)

wherein
$R^1$-$R^3$ have the meanings given in claim 1 and A is a leaving group, with an optionally substituted compound of the formula (III),

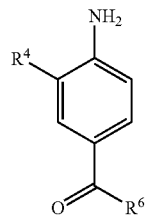
(III)

wherein
$R^4$ has the meaning given in claim 1 and
$R^6$ is OH, —O-methyl or —O-ethyl, to produce a compound of the formula (IV),

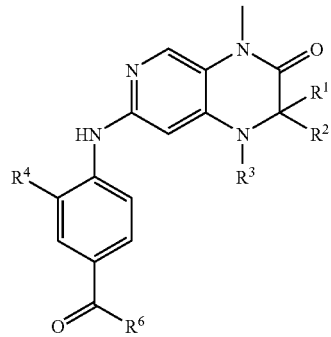
(IV)

wherein
$R^1$ to $R^4$ have the meanings given in claim 1 and
$R^6$ is —O-methyl or —O-ethyl,
hydrolyzing under suitable conditions the compound of the formula (IV) and reacting the product with an amine of the formula (V) under suitable conditions $$NH_2\text{-}L_n\text{-}R^5 \qquad (V)$$

wherein
$R^5$ has the meanings given in claim 1 to produce a compound of the formula (I).

8. A Compound of formula (II),

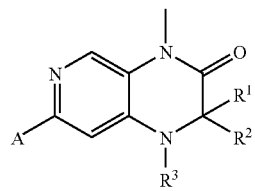
(II)

wherein
$R^1$, $R^2$ which may be identical or different denote hydrogen or a group selected from among $C_1$-$C_6$-alkyl optionally substituted by fluorine, $C_2$-$C_6$-alkenyl optionally substituted by fluorine, and $C_2$-$C_6$-alkynyl optionally substituted by fluorine, or
$R^1$ and $R^2$ together denote a 2- to 5-membered alkyl bridge,
$R^3$ denotes hydrogen or a group selected from among $C_1$-$C_{12}$-alkyl optionally substituted by fluorine, $C_2$-$C_{12}$-alkenyl optionally substituted by fluorine, $C_2$-$C_{12}$-alkynyl optionally substituted by fluorine, and $C_6$-$C_{14}$-aryl optionally substituted by one or more groups selected from OH, $NO_2$, CN, OMe, —$OCHF_2$, —$OCF_3$, —$NH_2$, halogen and $C_1$-$C_{10}$-alkyl, or a group selected from among $C_3$-$C_{12}$-cycloalkyl optionally substituted by one or more groups selected from OH, $NO_2$, CN, OMe, —$OCHF_2$, —$OCF_3$, —$NH_2$, halogen, $C_1$-$C_{10}$-alkyl, —O—$C_1$-$C_3$-alkyl, —COOH, —COO—$C_1$-$C_4$-alkyl and —$CONH_2$, $C_3$-$C_{12}$-cycloalkenyl, $C_7$-$C_{12}$-polycycloalkyl, $C_7$-$C_{12}$-polycycloalkenyl and $C_5$-$C_{12}$-spirocycloalkyl, and A is a leaving group.

9. A pharmaceutical composition comprising a compound according to claim 1 or a physiologically acceptable salt thereof, combined with conventional excipients and/or carriers, wherein the compound is 0.1 to 90% by weight of the composition.

10. The pharmaceutical composition according to claim 6, wherein the pharmaceutical composition is administered at a dose of 80 to 100 mg.

11. A pharmaceutical solution comprising a compound according to claim 1 or a physiologically acceptable salt thereof, combined with a liquid carrier, optionally combined with conventional excipients.

12. A pharmaceutical solution comprising a compound according to claim 1 or a physiologically acceptable salt thereof, combined with a liquid carrier, wherein the pharmaceutical solution is administered intravenously at a dose from 1 to 1000 mg of compound per hour.

13. The compound of formula (II) according to claim 8, wherein the leaving group A is selected from O-methyl, —SCN, fluorine, chlorine, bromine, iodine, methanesulphonyl, trifluoromethanesulphonyl and p-toluenesulphonyl.

* * * * *